(12) United States Patent
Fisher et al.

(10) Patent No.: US 10,246,746 B2
(45) Date of Patent: Apr. 2, 2019

(54) PRESERVING GENOMIC CONNECTIVITY INFORMATION IN FRAGMENTED GENOMIC DNA SAMPLES

(71) Applicant: ILLUMINA, INC., San Diego, CA (US)

(72) Inventors: Jeffrey S. Fisher, San Diego, CA (US); Frank J. Steemers, Encinitas, CA (US); Sasan Amini, Redwood City, CA (US); Kevin L. Gunderson, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 519 days.

(21) Appl. No.: 14/572,556

(22) Filed: Dec. 16, 2014

(65) Prior Publication Data

US 2015/0176071 A1 Jun. 25, 2015

Related U.S. Application Data

(60) Provisional application No. 61/935,776, filed on Feb. 4, 2014, provisional application No. 61/919,529, filed on Dec. 20, 2013.

(51) Int. Cl.
*C12Q 1/68* (2018.01)
*C12Q 1/6874* (2018.01)

(52) U.S. Cl.
CPC .................. *C12Q 1/6874* (2013.01)

(58) Field of Classification Search
None
See application file for complete search history.

(56) References Cited

U.S. PATENT DOCUMENTS

| | | |
|---|---|---|
| 5,130,238 A | 7/1992 | Malek |
| 5,185,243 A | 2/1993 | Ullman et al. |
| 5,223,414 A | 6/1993 | Zarling et al. |
| 5,455,166 A | 10/1995 | Walker |
| 5,573,907 A | 11/1996 | Carrino et al. |
| 5,599,675 A | 2/1997 | Brenner |
| 5,641,658 A | 6/1997 | Adams et al. |
| 5,679,524 A | 10/1997 | Nikiforov et al. |
| 5,750,341 A | 5/1998 | Macevicz |
| 5,858,671 A | 1/1999 | Jones |
| 5,965,443 A | 10/1999 | Reznikoff et al. |
| 6,210,891 B1 | 4/2001 | Nyren et al. |
| 6,214,587 B1 | 4/2001 | Dattagupta |
| 6,258,568 B1 | 7/2001 | Nyren |
| 6,261,782 B1 | 7/2001 | Lizardi |
| 6,274,320 B1 | 8/2001 | Rothberg et al. |
| 6,355,431 B1 | 3/2002 | Chee et al. |
| 6,383,754 B1 | 5/2002 | Kaufman |
| 6,437,109 B1 | 8/2002 | Reznikoff et al. |
| 6,593,113 B1 | 7/2003 | Tenkanen et al. |
| 6,777,187 B2 | 8/2004 | Makarov et al. |
| 6,828,098 B2 | 12/2004 | Langmore et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,138,267 B1 | 11/2006 | Jendrisak et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,537,897 B2 | 5/2009 | Brenner et al. |
| 7,582,420 B2 | 9/2009 | Oliphant et al. |
| 7,595,883 B1 | 9/2009 | El Gamal et al. |
| 7,611,869 B2 | 11/2009 | Fan |
| 7,670,810 B2 | 3/2010 | Gunderson et al. |
| 7,741,463 B2 | 6/2010 | Gormley |
| 8,003,354 B2 | 8/2011 | Shen et al. |
| 8,563,477 B2 | 10/2013 | Smith et al. |
| 2001/0046669 A1 | 11/2001 | McCombie et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2004/0110191 A1 | 6/2004 | Winkler et al. |
| 2004/0259229 A1 | 12/2004 | Thevelein et al. |
| 2005/0191698 A1 | 9/2005 | Chee et al. |
| 2006/0024681 A1 | 2/2006 | Smith et al. |

(Continued)

FOREIGN PATENT DOCUMENTS

| | | |
|---|---|---|
| EP | 03/20308 | 11/1993 |
| EP | 03/36731 | 5/1994 |

(Continued)

OTHER PUBLICATIONS

Sipos et al. (PLOS One, 2012, 7(8):1-9).*
Schevchenko et al. (Nucleic Acids Research, 2002, 30(11):2469-2477).*
Shendure et al. (Science, 2005, vol. 305:1728-1732).*
EPO communication pursuant to Article 94(c) EPC, dated Oct. 28, 2014, for Application No. 11802179.9.
International Preliminary Report on Patentability mailed in PCT application No. PCT/IB2014/000610, dated Jul. 14, 2015.
EP Communication pursuant to Article 94(3) EPC in 12741945.5 dated Oct. 26, 2015.
"GS FLX Titanium LV emPCR Kit (Lib-L) protocol", Aug. 2008, 1-2.

(Continued)

*Primary Examiner* — Stephanie K Mummert
(74) *Attorney, Agent, or Firm* — Fletcher Yoder, P.C.

(57) ABSTRACT

A method of sequencing a target nucleic acid polymer by (a) modifying a target nucleic acid polymer to produce a modified nucleic acid polymer; (b) producing fragments of the modified nucleic acid polymer, wherein the fragments are attached to locations on a solid support surface (c) determining nucleotide sequences from the fragments at the locations; and (d) producing a representation of the nucleotide sequence for the target nucleic acid polymer based on the nucleotide sequences from the fragments and the relative distances between the locations on the solid support surface.

36 Claims, 11 Drawing Sheets

Specification includes a Sequence Listing.

(56) References Cited

U.S. PATENT DOCUMENTS

| | | |
|---|---|---|
| 2006/0040297 A1 | 2/2006 | Leamon et al. |
| 2006/0216309 A1 | 9/2006 | Holden |
| 2006/0292611 A1 | 12/2006 | Berka et al. |
| 2007/0128610 A1 | 6/2007 | Buzby |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2008/0234136 A1 | 9/2008 | Drmanac et al. |
| 2008/0242560 A1 | 10/2008 | Gunderson et al. |
| 2009/0026082 A1 | 1/2009 | Rothberg et al. |
| 2009/0032401 A1 | 2/2009 | Ronaghi et al. |
| 2009/0047680 A1 | 2/2009 | Lok |
| 2009/0127589 A1 | 5/2009 | Rothberg et al. |
| 2009/0176234 A1 | 7/2009 | Dramanac et al. |
| 2010/0022403 A1 | 1/2010 | Kurn et al. |
| 2010/0069263 A1 | 3/2010 | Shendure et al. |
| 2010/0111768 A1 | 5/2010 | Banerjee et al. |
| 2010/0120098 A1 | 5/2010 | Grunenwald et al. |
| 2010/0137143 A1 | 6/2010 | Rothberg et al. |
| 2010/0282617 A1 | 11/2010 | Rothberg |
| 2011/0014657 A1 | 1/2011 | Rigatti et al. |
| 2011/0059865 A1 | 3/2011 | Smith et al. |
| 2011/0311506 A1 | 12/2011 | Craig et al. |
| 2012/0053063 A1 | 3/2012 | Rigatti et al. |
| 2012/0129704 A1 | 5/2012 | Gunderson et al. |
| 2012/0208724 A1 | 5/2012 | Steemers |
| 2012/0208705 A1 | 8/2012 | Steemers |
| 2012/0270305 A1 | 10/2012 | Reed et al. |
| 2013/0203605 A1 | 8/2013 | Shendure et al. |
| 2013/0338042 A1 | 12/2013 | Shen et al. |
| 2014/0079923 A1 | 3/2014 | George et al. |
| 2014/0093916 A1 | 4/2014 | Belyaev |

FOREIGN PATENT DOCUMENTS

| | | | |
|---|---|---|---|
| EP | 04/39182 | 4/1996 | |
| EP | 2712931 | 4/2014 | |
| WO | 89/09835 | 10/1989 | |
| WO | 89/10977 | 11/1989 | |
| WO | 89/12696 | 12/1989 | |
| WO | 90/01069 | 2/1990 | |
| WO | 1991/006678 | 5/1991 | |
| WO | 95/23875 | 9/1995 | |
| WO | 1998/44151 | 10/1998 | |
| WO | 2004/018497 | 3/2004 | |
| WO | 2004/042078 | 5/2004 | |
| WO | 2005/065814 | 7/2005 | |
| WO | 2005/100585 | 10/2005 | |
| WO | 2007/098279 | 8/2007 | |
| WO | 2007/123744 | 11/2007 | |
| WO | 2010/002883 | 1/2010 | |
| WO | 2010/048605 | 4/2010 | |
| WO | 2012/025250 | 3/2012 | |
| WO | WO2012025250 | * 3/2012 | ............... C12Q 1/68 |
| WO | 2012/058096 | 5/2012 | |
| WO | 2012/061832 | 5/2012 | |
| WO | 2012/103545 | 8/2012 | |
| WO | 2012/106546 | 8/2012 | |
| WO | 2013/177220 | 11/2013 | |
| WO | 2013/184796 | 12/2013 | |
| WO | 2014/142850 | 9/2014 | |

OTHER PUBLICATIONS http://www_epibio_com_nextera.
International Search Report and Written Opinion for PCT/US12/23679, Applicant: University of Washington Through Its Center for Commercialization, dated Aug. 24, 2012.
"International Search Report and the Written Opinion", issued for PCT/US2011/059642, dated Apr. 10, 2012, 12 pgs.
Invitation to Pay Additional fees in PCT/US2014/070658 dated Mar. 31, 2015.
Office Action issued for U.S. Appl. No. 12/559,124 dated Mar. 27, 2012, 13 pages.
PCT Search Report mailed in PCT application No. PCT/US2014/070658, dated Jun. 26, 2015.
Supplementary European Search Report for Application EP12741945.5, Applicant: University of Washington Through Its Center for Commercialization, dated Sep. 22, 2014.
Adey, "Rapid, low-input, low-bias construction of shotgun fragment libraries by high-density in vitro transposition", Genome Biology 11 r119, Dec. 8, 2010, 47 pages.
Adey, et al., "Ultra-low-input, tagmentation-based whole-genome bisulfite sequencing", vol. 22, No. 6, Mar. 30, 2012 (Mar. 30, 2012), XP055136909; ISN: 1088-9051, DOI: 10.1101/gr.136242.111, the whole document, 1139-1143.
Adey, et al., "Rapid, low-input, low-bias construction of shotgun fragment libraries by high-density in vitro transposition", Genome Biology vol. 11(12), 2010, R119.
Bains, et al., "A novel method for nucleic acid sequence determination", J. Theor Biol., 135(3), 1998, 303-307.
Ball et al., "Targeted and genome-scale strategies reveal gene-body methylation signatures in human cells", Nat Biotechnol 27(4), 2009, 361-368.
Bansal et al., "An efficient and accurate algorithm for the haplotype assembly problem", Bioinformatics;24(16), 2008, i153-9.
Batzoglou, et al., "ARACHNE: a whole-genome shotgun assembler", Genome Research, 12(1), 2002, 177-189.
Benetti et al., "A mammalian microRNA cluster controls DNA methylation and telomere recombination via Rbl2-dependent regulation of DNA methyltransferases.", Nat Struct Mol Bioi 15(3), 2008, 268-279.
Bentley, et al., "Accurate whole human genome sequencing using reversible terminator chemistry", Nature, vol. 456, No. 7218, Nov. 6, 2008, 53-59.
Bimber, et al., "Whole-genome characterization of human and simian immunodeficiency virus intrahost diversity by uptradeep pyrosequencing", Journal of Virology, vol. 84, No. 22, 2010, 12087-12092.
Bloch, et al., "Purification of *Escherichia coli* chromosomal segements without cloning", Biochemical and Biophysical Research Communications, vol. 223, 1996, 104-111.
Boeke, et al., "Transcription and reverse transcription of retrotransposons", Annu Rev Microbiol 43, 1989, 403-34.
Branton, et al., "The potential and challenges of nanopore sequencing", Nature Biotechnology, vol. 26, No. 10, Oct. 2008, 1146-1153.
Braslavsky, et al., "Sequence information can be obtained from single DNA molecules", PNAS, 100(7). Epub Mar. 21, 2003, Apr. 1, 2003, 3960-3964.
Brown, et al., "Retroviral Integration: Structure of the Initial Covalent Product and Its Precursor, and a Role for the Viral IN Protein", PNAS, 86, 1989, 2525-9.
Brownlie, et al., "The Caenorhabditis briggsae genome contains active CbmaT1 and Tcb1 transposons", Molecular Genetics and Genomics, vol. 273, 2005, 92-101.
Caruccio, Nicholas et al., "Preparation of next-generation sequencing libraries using Nextera(TM) technology: simultaneous DNA fragmentation and adaptor tagging by in vitro transpoition", Methods in Molecular Biology, 733, Jan. 1, 2011, 241-255.
Chernoff, et al., "Molecular Analysis of the von Hippel-Lindau Disesase Gene", Methods. Mol. Med. 53, 2001, 193-216.
Chinese Office Action, "Application No. 201280012945.4", dated Apr. 17, 2015.
Chinese Office Action, "Application No. CN201280012945.4", dated May 28, 2014.
Clark, et al., "High sensitivity mapping of methylated cytosines", Nucleic Acids Research, vol. 22, No. 15, 1994, 2990-2997.
Cockroft, et al., "A single-molecule nanpore device detects DNA polymerase activity with single-nucleotide resolution", J. Am. Chem. Soc, 130(3), 2008, 818-820.
Cokus et al., "Shotgun bisulphite sequencing of the *Arabidopsis* genome reveals DNA methylation patterning", Nature 452.7184, 2008, 215-219.
Colegio, et al., "In vitro transposition system for efficient generation of random mutants of Campylobacter jejuni", J. Bacteriol, 183, 2001, 2384-8.

(56) References Cited

OTHER PUBLICATIONS

Craig, "Transposon Tn7", Review in: Curr Top Microbiol Immunol, 204, 1996, 27-48.
Craig, "V(D)J recombination and transposition: closer than expected", Science, 271, 1996, 1512.
De Vries, et al., "PCR on Cell Lysates Obtained from Whole Blood Circumvents DNA Isolation", Clin. Chem. 47, 2001, 1701-1702.
Deamer, et al., "Characterization of nucleic acids by nanopore analysis", ACC Chem Res, 35(10), 2002, 817-825.
Deamer, et al., "Nanopores and nucleic acids: prospects for ultrarapid sequencing", Trends Biotechnol, 18(4), 2000, 147-151.
Dean, et al., "Comprehensive human genome amplification using multiple displacement amplification", PNAS, 99, 2002, 5261-5266.
Deng et al., "Targeted bisulfite sequencing reveals changes in DNA methylation associated with nuclear reprogramming.", Nat Biotechnol 27(4), 2009, 353-360.
Down et al., "A Bayesian deconvolution strategy for immunoprecipitation-based DNA methylome analysis.", Nat Biotechnol 26(7), 2008, 779-785.
Dressman, et al., "Transforming single DNA molecules into fluorescent magnetic particles for detection and enumeration of genetic variations", PNAS, 100(15), 2003, 8817-8822.
Drmanac, et al., "Accurate sequencing by hybridization for DNA diagnostics and individual genomics", Nature Biotechnology, 16(1), 1998, 54-58.
Drmanac, et al., "Human genome sequencing using unchained base reads on self-assembling DNA nanoarrays", Science.2009; 327(5961), 2009, 78-81.
Duan et al., "A three-dimensional model of the yeast genome", Nature; 465(7296), 2010, 363-7.
Duitama, et al., Proceedings of the First ACM International Conference on Bioinformatics and Computational Biology, 160-169, 2010.
Eid, J. et al., "Real-Time DNA Sequencing from Single Polymerase Molecules", Science 323,, 2009, 133-138.
Ewing, et al., "Base-calling of automated sequencer traces using phred. II. Error probabilities", Genome Research, 8, 1998, 186-194.
Fan et al., "Whole-genome molecular haplotyping of single cells.", Nat Biotech 29(1):, 2011, 51-57.
Fodor, "Light-Directed, Spatially Addressable Parallel Chemical Synthesis", Science, vol. 251, 1991, 767-773.
Fullwood, Melissa J. et al., "Chromatin interaction analysis using paired-end tag sequencing", Current Protocols in Molecular Biology, Supplement 89, Jan. 21, 2010, 21.15.1-21.15.25.
Fullwood et al., "An oestrogen-receptor-bound human chromatin interactome", Nature 462, 2009, 58-64.
Gal, et al., "Directional cloning of native PCR products with preformed sticky ends (autosticky PCR)", Molecular & General Genetics, vol. 260, No. 6, Jan. 1999, 569-573.
Geiss et al., "Direct multiplexed measurement of gene expression with colorcoded probe pairs", Nat Biotechnol.; 26(3), 2008, 317-25.
Gloor, "Gene targeting in *Drosophila*", Methods Mol Biol. 260, 2004, 97-114.
Gnerre et al., "High-quality draft assemblies of mammalian genomes from massively parallel sequence data", Proc Natl Acad Sci USA., [Epub ahead of print] PubMed PMID: 21187386, Dec. 27, 2010.
Goodman, et al., "Identifying genetic determinants needed to establish a human gut symbiont in its habitat", Cell Host & Microbe, vol. 6, Sep. 2009, 279-289.
Goryshin, et al., "Tn5 in vitro transposition", J. Biol. Chem. 273, 1998, 7367-74.
Goryshin, et al., "Tn5 in Vitro Transposition*", vol. 273, No. 13, Issue of Mar. 27, 1998, 7367-7374.
Grunenwald, et al., "Rapid, high-throughput library preparation for next-generation sequencing, Nature Methods, Application Notes", Aug. 2010, iii-iv.
Grunenwald et al., "Nextera PCR-Free DNA Library Preparation for Next-Generation Sequencing", (Poster Presentation, AG8T)., 2011.

GU et al., "Preparation of reduced representation bisulfite sequencing libraries for genome-scale DNA methylation profiling", Nat Protoc 6(4), 2011, 468-481.
Haapa, et al., "An efficient and accurate integration of mini-Mu transposons in vitro: a general methodology for functional genetic analysis and molecular biology applications", Nucleic Acids Research vol. 27, No. 13, 1999, 2777-2784.
Handelsman, J. et al., "Metagenomics: Application of Genomics to Uncultured Microorganisms", Microbiology and Molecular Biology Reviews, 68(4), Dec. 2004, 669-685.
Harris, et al., "Comparison of sequencing-based methods to profile DNA methylation and identification of monoallelic epigenetic modifications.", Nat Biotechnol 28(10), 2010, 1097-1105.
Healy, "Nanopore-based single-molecule DNA analysis", Nanomed. 2(4), 2007, 459-481.
Heredia, et al., "In vitro double transposition for DNA identification", Analytical Biochemistry 399, 2010, 78-83.
Hiatt et al., "Tag-directed assembly of locally derived short sequence reads", Nat Methods. 7(2), 2010, 119-22.
Ichikawa, et al., "In vitro transposition of transposon Tn3", J Biol Chem, 265, 1990, 18829-32.
Jackson, et al., "Plasmid tagging for efficient large-scale sequence completion of entire clone inserts", BioTechniques, vol. 34, Mar. 2003, 604-608.
Johnson et al., "Genome-wide mapping of in vivo protein-DNA interactions", Science. 316(5830)., 2007, 1497-502.
Joos, et al., "Covalent attachment of hybridizable oligonucleotides to glass supports", Analytical Biochemistry, 247, 1997, 96-101.
Keith, et al., "Algorithms for Sequence Analysis via Mutagenesis", Bioinformatics, vol. 20 No. 15; published online doi:10.1093/bioinformatics/bth258, May 14, 2004, 2401-2410.
Keith, et al., "Unlocking Hidden Genomic Sequence", Nucleic Acids Research, vol. 32, No. 3, published online DOI: 10.1093/nar/gnh022, Feb. 18, 2004, e35.
Kidd et al., "Mapping and sequencing of structural variation from eight human genomes", Nature. 453 (7191), 2008, 56-64.
Kirby, et al., "Cryptic plasmids of *Mycobacterium avium*L Tn552 to the rescue", Molecular Microbiology, 43, 2002, 173-86.
Kirby, J.R. "In vivo mutagenesis using Ez-Tn5TM.", Methods in Enzymology, vol. 421, 2007, 17-21.
Kitzman, et al., "Haplotype-resolved genome sequencing of a Gujarati Indian individual", Nature Biotechnology, vol. 29(1), Jan. 2011, 59-63.
Kleckner, et al., "Tn10 and IS10 transposition and chromosome rearrangements: mechanism and regulation in vivo and in vitro", Curr Top Microbiol Immunol., 204, 1996, 49-82.
Korlach, et al., "Selective aluminum passivation for targeted immobilization of single DNA polymerase molecules in zero-mode waveguide nanostructures", PNAS, 105(4), 2008, 1176-1181.
Kramer, "cDNA Library Construction from Single Cells", Current Protocols in Neuroscience, 2002, 4.27.1-4.27.19.
Lage, Jose M. et al., "Whole genome analysis of genetic alterations in small DNA samples using hyperbranched strand displacement amplification and array-CGH", Genome Research, vol. 13., Issue 2, Feb., Feb. 2003, 294-307.
Lai et al., "A shotgun optical map of the entire Plasmodium falciparum genome", Nat Genet. 23(3), 1999, 309-13.
Lampe, et al., "A purified mariner transposase is sufficient to mediate transposition in vitro", EMBO J., 15, 1996, 5470-5479.
Lander, et al., "Initial sequencing and analysis of the human genome", Nature, 409(6822), 2001, 860-921.
Levene, et al., "Zero-Mode Waveguides for Single-Molecule Analysis at high concentrations", Science 299, 2003, 682-686.
Levy, et al., "The Diploid Genome Sequence of an Individual Human", PLoS Biology, vol. 5, Issue 10, Oct. 2007, 2113-2144.
Li, et al., "DNA molecules and configurations in a solid-state nanopore microscope", Nature Mater, 2(9), 2003, 611-615.
Li, et al., "Fast and accurate short read alignment with Burrows-Wheeler transform", Bioinformatics 25:1754-1760, 2009.
Li et al., "De novo assembly of human genomes with massively parallel short read sequencing", Genome Res. 20 (2), 2010, 265-72.
Li et al., "Primasebased whole genome amplification", Nucleic Acids Res. 36(13), 2008, e79.

(56) References Cited

OTHER PUBLICATIONS

Li et al., "The DNA methylome of human peripheral blood mononuclear cells", PLoS Biol 8(11), 2010, e1000533.
Lieberman-Aiden et al., "Comprehensive mapping of long-range interactions reveals folding principles of the human genome", Science. 326(5950), 2009, 289-93.
Lim et al., "Shotgun optical maps of the whole *Escherichia coli* 0157:H7 genome", Genome Res. 11(9), 2001, 1584-93.
Lin et al., "Wholegenome shotgun optical mapping of Deinococcus radiodurans.", Science. 285(5433):, 1999, 1558-62.
Lister et al., "Human DNA methylomes at base resolution show widespread epigenomic differences", Nature, 462(7271), Nov. 19, 2009, 315-322.
Lizardi, "Mutation detection and single-molecule counting using isothermal rolling-circle amplification", Nature Genetics, vol. 19, 1998, 225-232.
Lundquist, et al., "Parallel confocal detection of single molecules in real time", Opt. Lett. 33(9), 2008, 1026-1028.
Mardis, E.R. "The impact of next-generation sequencing technology on genetics", Trends in Genetics 24, 2008, 133-141.
Margulies, et al., "Genome sequencing in microfabricated high-density picolitre reactors", Nature, vol. 437, 2005, 376-380 and Supplemental Materials.
Marine, et al., "Evaluation of a transposase protocol for rapid generation of shotgun high-throughput sequencing libraries from nanogram quantities of DNA", Appl. Environ. Microbiol, vol. 77 (22), Nov. 2011, 8071-8079.
Mazutis et al., "Droplet-based microfluidic systems for high-throughput single DNA molecule isothermal amplification and analysis", Anal Chern. 81 (12), 2009, 4813-21.
McCloskey, et al., "Encoding PCR Products with Batch-stamps and Barcodes", Biochem Genet 45:761, Oct. 23, 2007, 761-767.
Meissner, et al., Nucleic Acids Research, 33, 2005, 5868-5877.
Miner, et al., "Molecular barcodes detect redundancy and contamination in hairpin-bisulfite PCR", Nucleic Acids Research, 2004, vol. 32, No. 17, Sep. 30, 2004, e135, 4 pages.
Mitra, Robi D. et al., "Fluorescent in situ sequencing on polymerase colonies", Analytical Biochemistry—320 (2003) 55-65, 2003, 55-65.
Mizuuchi, "In vitro transposition of bacteriophase Mu: a biochemical approach to a novel replication reaction", Cell, 35, 1983, 785-94.
Mizuuchi, Kiyoshi "Transpositional Recombination: Mechanistic Insights from Studies of Mu and Other Elements", Annu. Rev. Biochem. 61, 1992, 1011-51.
Mortazavi, Ali et al., "Mapping and quantifying mammalian transcriptomes by RNA-seq", Nature Methods, 5(7), 2008, 621-8.
Ng, et al., "Targeted capture and massively parallel sequencing of 12 human exomes", Nature. 461 (7261), 2009, 272-6.
Nijman, et al., "Mutation discovery by targeted genomic enrichment of multiplexed barcoded samples", Nature Methods, vol. 7, No. 11, Nov. 2010, 913-915.
Oh, et al., "A universal TagModule collection for parallel genetic analysis of microorganisms", Nucleic Acids Research, vol. 38, No. 14, May 21, 2010, 146.
Oh, J. et al., "A Robust Platform for High-Throughput Genomics in Microorganisms", A dissertation submitted to the department of genetics and the committee on graduate studies of Stanford University in partial fulfillment of the requirements for the degree of doctor of philosophy, Mar. 2010, i, ii and 10-30.
Ohtsubo, et al., "Bacterial insertion sequences", Curr. Top. Microbiol. Immunol. 204, 1996, 1-26.
Ooka, et al., "Inference of the impact of insertion sequence (IS) elements on bacterial genome diversification through analysis of small-size structural polymorphisms in *Escherichia coli* O157 genomes", Genome Research, vol. 19, 2009, 1809-1816.
Oroskar, et al., "Detection of immobilized amplicons by ELISA-like techniques", Clinical Chemistry 42, 1996, 1547-1555.
Paul, et al., "Single-molecule dilution and multiple displacement amplification for molecular haplotyping", BioTechniques 38, Apr. 2005, 553-559.
Plasterk, "The Tc1/mariner transposon family", Curr Top Microbiol Immunol, 204, 1996, 125-43.
Pobigaylo, et al., "Construction of a large signature-tagged minOTn5 transposon library and its application to mutagenesis of Sinorhizobium meliloti", Applied and Environmental Microbiology, vol. 72, No. 6, Jun. 2006, 4329-4337.
Ramanathan, et al., "An integrative approach for the optical sequencing of single DNA molecules", Analytical Biochemistry, vol. 330, No. 2, 2004, 227-241.
Reinhardt, J.A. et al., "De Novo Assembly Using Low-Coverage Short Read Sequence Data from the Rice Pathogen *Pseudomonas Syringae* pv. *Oryzae*", Genome Research 19(2), Feb. 2009, 294-305.
Riehn et al., "Restriction mapping in nanofluidic devices.", Proceedings of the National Academy of Sciences of the United States of America 102(29):, 2005, 10012-10016.
Ritz, "Structural variation analysis with strobe reads", Bioinformatics. 26(10), 2010, 1291-8.
Ronaghi, M. et al., "A Sequencing Method Based on Real-Time Phyrophosphate", Science. Jul. 17, 1998; 281 (5375):363-365 USE, Jul. 17, 1998, 363-365.
Ronaghi, M. et al., "Real-time DNA sequencing using detection of pyrophosphate release", Anal. Biochem. Nov. 1, 1996; 242 (1):84-9, Nov. 1, 1996, 84-89.
Ronaghi, Mostafa "Pyrosequencing sheds light on DNA sequencing", Genome Res, 11(1), 2001, 3-11.
Savilahti, et al., "The Phage Mu transpososome core: DNA requirements for assembly and function", EMBO J., 14, 1995, 4893-4903.
Schwartz, et al., "Capturing native long-range contiguity by in situ library construction and optical sequencing", PNAS, vol. 109m No. 46, 2012, 18749-18754.
Schwartz et al., "Ordered restriction maps of *Saccharomyces cerevisiae* chromosomes constructed by optical mapping", Science. 262 (5130), 1993, 110-4.
Shendure, et al., "Accurate Multiplex Polony Sequencing of an Evolved Bacterial Genome", Science, vol. 309, Sep. 9, 2005, 1728-1732.
Shendure, et al., "Advanced sequencing technologies: methods and goals", Nature Rev. Genet., 5, 2004, 335-344.
Shendure, et al., "Next-generation DNA sequencing", Nature Biotechnology 26(10), 2008, 1135-1145.
Shendure, "Sequence Tag Directed Subassembly of Short Sequencing Reads Into Long Sequencing Reads", U.S. Appl. No. 61/096,720, filed Sep. 12, 2008.
Shevchenko, et al., "Systematic sequencing of cDNA clones using the transposon Tn5", Nacl. Acids Res. 30, 2002, 2469-2477.
Sipos, et al., "An Improved Protocol for Sequencing of Repetitive Genomic Regions and Structural Variations Using Mutagenesis and Next Generation Sequencing", PLoS One 7(8), published online doi:10.1371/journal.pone.0043359, Aug. 17, 2012, e43359.
Smith, et al., "Direct Mechanical Measurements of the Elasticity of Single DNA Molecules by Using Magnetic Beads", Science, 258, 1992, p. 1122.
Soni, et al., "Progress toward Ultrafast DNA Sequencing Using Solid-State Nanopores", Clin Chem, 53(11), 2007, 1996-2001.
Sorber, K. et al., "The Long March: A Sample Preparation Technique That Enhances Contig Length and Coverage by High-Throughput Short-Read Sequencing", PLoS ONE 2(10):e3495, Oct. 2008, 9 pages.
Steensel et al., "Genomics tools for unraveling chromosome architecture", Nature Bitoechnology, Oct. 13, 2010.
Syed, "Next-generation sequencing library preparation: simultaneous fragmentation and tagging using in vitro transposition", Application Notes, Nature Methods, Epicentre Biotech, Nov. 2009, i-ii.
Syed, Fraz et al., "Optimized library preparation method for next-generation sequencing", Nature Methods, 6(10), 2009, I-II.
Taylor, et al., "Characterization of chemisorbed monolayers by surface potential measurements", J. Phys. D: Appl. Phys., 24, 1991, p. 1443.
Van Berkum et al., "Method to Study the Three-dimensional Architecture of Genomes", http://www.jove.com/details.stp?id=1869 doi:10.3791/1869. J Vis Exp.39, (2010).
Vincent, et al., "Helicase-dependent isothermal DNA amplification", EMBO Rep 5, 2004, 795-800.

(56) References Cited

OTHER PUBLICATIONS

Walker, et al., "A Chemiluminescent DNA Probe Test Based on Strand Displacement Amplification", Molecular Methods for Virus Detection, 1995, Academic Press Inc. Ch 15 pp. 329-349., 1995, 329-349.

Walker, et al., "Strand displacement amplification—an isothermal, in vitro DNA amplification technique", NAR, 20, 1992, 1691-1696.

Wang, Haoyi et al., "Calling Cards enable multiplexed identification of genomic targets of DNA-binding proteins", Genome Research, vol. 21, No. 5, 2011, 748-755.

Waterston et al., "Initial sequencing and comparative analysis of the mouse genome", Nature. 420(6915), 2002, 520-62.

Waterston et al., "On the sequencing of the human genome", Pro Proc Natl Acad Sci USA. 99(6), 2002, 3712-6.

Wilson, et al., "New transposon delivery plasmids for insertional mutagenesis in *Bacillus anthracis*", Journal of Microbiological Methods, 71, 2007, 332-335.

Wold, B. et al., "Sequence Census Methods for Functional Genomics", Nature Methods, 5(1), Jan. 2008, 19-21.

Xu, J. "Extracting Haplotypes from Diploid Organisms", Current Issues in Molecular Biology, vol. 8, Jul. 2006, 113-122.

Zeevi, et al., "Increasing cloning possibilities using artificial zinc finger nucleases", Proceedings of the National Academy of Sciences, USA, vol. 105, Nov. 35, Sep. 2008, 12785-12790.

Zeng et al., "High-performance single cell genetic analysis using microfluidic emulsion generator arrays.", Anal Chem. 82 (8), 2010, 3183-90.

Zerbino D.R., et al., "Velvet: Algorithms for De Novo Short Read Assembly Using de Bruijn Graphs", Genome Research, 18(5), Mar. 2008, 821-829.

Zhang, et al., "A Novel Mechanism of Transposon-Mediated Gene Activation", PLoS Genetics e1000689. Epub Oct. 16, 2009.

Zhou, et al., "Molecular genetic analysis of tarnsposase—end DNA sequence recognition: Cooperativity of three adjacent base-pairs in specific interaction with a mutant Tn5 transposase", Journal of Molecular Biology, vol. 276, 1998, 913-925.

Zhou et al., "A Single Molecule Scaffold for the Maize Genome", PLoS Genet 5(11), 2009, e1000711.

Zhou et al., "Validation of rice genome sequence by optical mapping", BMC Genomics 8(1), 2007, 278.

Zilberman et al., "Genome-wide analysis of DNA methylation patterns.", Development 134(22), 2007, 3959-3965.

Mardis et al., "Next-generation DNA sequencing methods," Annu. Rev. Genomics Hum. Genet. 2008, 9, 387-402.

Peck et al., "A method for high-throughput gene expression signature analysis," Genome Biology 2006, 7(7), Article R61, 6 pages.

Raymond et al., "Targeted, haplotype-resolved resequencing of long segments of human genome," Genomics 2005, 86, 759-766.

Seong et al., "Measurement of enzyme kinetics using a continuous-flow microfluidic system," Anal. Chem. 2003, 75(13), 3161-3167.

Simon et al., "Short-Read Sequencing Technologies for Transcriptional Analyses," Annu. Rev. Plant Biol. 2009, 60, 305-333.

Wong et al., "ChIP'ing the mammalian genome: technical advances and insights into functional elements," Genome Med. 2009, 1, 89, 10 pages.

Khandjian, E.W. et al., "UV Crosslinking of RNA to Nylon Membrane Enhances Hybridization Signals," Mol. Biol. Rep. 1986, 11, 107-115.

* cited by examiner

A

B

C

SEQUENCE LISTING

```
<160> NUMBER OF SEQ ID NOS: 4

<210> SEQ ID NO 1
<211> LENGTH: 35
<212> TYPE: DNA
<213> ORGANISM: Homo sapiens

<400> SEQUENCE: 1
cttaaaaaga gcatgtttta ccttttgtaa attat                          35
```

```
<210> SEQ ID NO 2
<211> LENGTH: 35
<212> TYPE: DNA
<213> ORGANISM: Homo sapiens

<400> SEQUENCE: 2
cttaaaaaga gcatgtttta cctttttgtaa attat                                35

<210> SEQ ID NO 3
<211> LENGTH: 16
<212> TYPE: DNA
<213> ORGANISM: Homo sapiens

<400> SEQUENCE: 3
gtaaattata tctcaa                                                      16

<210> SEQ ID NO 4
<211> LENGTH: 44
<212> TYPE: DNA
<213> ORGANISM: Homo sapiens

<400> SEQUENCE: 4
tacttaaaaa gagcatgttt tacattttgt aaattatatc tcaa                       44
```

PRESERVING GENOMIC CONNECTIVITY INFORMATION IN FRAGMENTED GENOMIC DNA SAMPLES

This application claims priority to U.S. Application Ser. No. 61/919,529, filed Dec. 20, 2013 and U.S. Application Ser. No. 61/935,776, filed Feb. 4, 2014, which are incorporated herein by reference.

BACKGROUND

This disclosure relates generally to sequencing nucleic acids, and more specifically to phasing, error correction and assembly of sequence information obtained from nucleic acids.

The efforts of the Human Genome Project opened a broader window to the human genetic code. The work to further unlock the human genome is ongoing, for example using high-throughput sequencing technologies. The Hap-Map (Haplotype Map) Project is a global scientific effort directed at discovering genetic variants that lead to disease by comparing genomic information from people who do and don't have the disease. Alleles, variable forms of a DNA sequence for a particular genetic locus, can contain one or more different genetic variants and identifying haplotypes, or combinations of alleles at different locations, or loci, on a particular chromosome is a main focus of the HapMap Project. Identified haplotypes where the two groups of people differ might correlate to locations of genetic anomalies that cause the disease being evaluated. As such, HapMap results will help to describe the common patterns of genetic variation in humans and whether those variations are potentially correlated to disease.

The information gained from these efforts is expected to provide a valuable tool in helping to decipher the causes or cures for many diseases and disorders. Unfortunately, the cost in performing such large scale sequencing is still very high and the technologies to provide more in depth information, such as single chromosome haplotyping, phasing of alleles or target sequences, have been elusive. Thus, there exists a need for additional tools and technologies to unlock more information from the human genome. The present disclosure addresses this need and provides other advantages as well.

BRIEF SUMMARY

The methods set forth in the present application can be useful for determining proximity of sequence fragments with respect to a larger target nucleic acid from which the fragments were derived. For example, the methods can be used to determine phasing and to identify haplotypes for a relatively long target nucleic acid sequence when individual sequence reads are shorter than the length of the target nucleic acid under evaluation.

The present disclosure provides a method of sequencing a target nucleic acid polymer. The method can include the steps of (a) modifying a target nucleic acid polymer to produce a modified nucleic acid polymer, wherein the modified nucleic acid polymer includes a plurality of sequence regions from the target nucleic acid polymer; (b) producing fragments of the modified nucleic acid polymer in a vessel having a solid support surface, each fragment comprising one of the sequence regions; (c) capturing the fragments randomly at locations in a region of the solid support surface; (d) determining nucleotide sequences of the sequence regions by detecting the fragments at the locations; and (e) producing a representation of the nucleotide sequence for the target nucleic acid polymer based on the nucleotide sequences from the fragments and the relative distances between the locations on the solid support surface.

Also provided is a method of sequencing a target nucleic acid polymer that includes the steps of (a) adding inserts into a target nucleic acid polymer to form a modified nucleic acid polymer including a plurality of internal inserts; (b) producing fragments of the modified nucleic acid polymer in a fluid that is in contact with a solid support surface, thereby releasing fragments that each include at least a portion of the inserts; (c) capturing the fragments from the fluid randomly at locations on a solid support surface; (d) determining nucleotide sequences from the fragments by detecting the fragments at the locations; and (e) producing a representation of the nucleotide sequence for the target nucleic acid polymer based on the nucleotide sequences from the fragments and the relative distances between the locations on the solid support surface.

This disclosure further provides a method of sequencing a target nucleic acid polymer, that includes the steps of (a) modifying a target nucleic acid polymer to produce a modified nucleic acid polymer, wherein the modified nucleic acid polymer includes a plurality of sequence regions from the target nucleic acid polymer; (b) attaching the modified nucleic acid polymer to a region on a solid support surface; (c) producing fragments of the modified nucleic acid polymer that is attached to the solid support surface, wherein the fragments are attached to locations at the region of the solid support surface; (d) determining nucleotide sequences from the fragments by detecting the fragments at the locations; and (e) producing a representation of the nucleotide sequence for the target nucleic acid polymers based on the nucleotide sequences from the fragments and the relative distances between the locations on the solid support surface.

Further provided is method of sequencing a target nucleic acid polymer that includes the steps of (a) adding inserts into a target nucleic acid polymer to form a modified nucleic acid polymer including a plurality of internal inserts; (b) attaching the modified nucleic acid polymer to a solid support surface; (c) producing fragments of the modified nucleic acid polymer that is attached to the solid support surface, wherein the fragments are attached to locations on the solid support surface and wherein the fragments each include at least a portion of the inserts; (d) determining nucleotide sequences from the fragments by detecting the fragments at the locations; and (e) producing a representation of the nucleotide sequence for the target nucleic acid polymer based on the nucleotide sequences from the fragments and the relative distances between the locations on the solid support surface.

The methods set forth in the present application can also be useful for determining the origin of sequence reads obtained for mixed samples. For example, the methods can be used to identify sequence fragments that are derived from a common organism when a mixture of target nucleic acids from a multiple organisms is processed as a mixture. Thus, the methods can be used to identify individual organisms in metagenomic samples. Other samples containing mixtures of target nucleic acids from different sources can also be used.

The present disclosure provides a method of determining the source for individual sequences in a mixture of sequences from different sources. The method can include the steps of (a) providing a mixture of target nucleic acid polymers from a plurality of different sources; (b) modifying the mixture of target nucleic acid polymers to produce a mixture of modified nucleic acid polymers, wherein the mixture of modified nucleic acid polymers includes a plurality of sequence regions from the different sources; (c) producing fragments of the modified nucleic acid polymers in a vessel having a solid support surface, each fragment comprising a sequence region from a single one of the different sources; (d) capturing the fragments randomly at locations of the solid support surface, under conditions wherein fragments from a common target nucleic acid polymer preferentially localize to proximal locations on the solid support surface; (e) determining nucleotide sequences of the fragments at the locations; and (f) identifying the nucleotide sequences that are derived from a common source in the plurality of different sources based on the nucleotide sequences from the fragments and the relative distances between the locations on the solid support surface.

Also provided is a method of determining the source for individual sequences in a mixture of sequences from different sources, wherein the method includes the steps of (a) providing a mixture of target nucleic acid polymers from a plurality of different sources; (b) adding inserts into the target nucleic acid polymers in the mixture to form a mixture of modified nucleic acid polymers, each polymer including a plurality of internal inserts; (c) producing fragments of the modified nucleic acid polymers in a fluid that is in contact with a solid support surface, thereby releasing fragments that each include at least a portion of each of the inserts; (d) capturing the fragments from the fluid randomly at locations on a solid support surface; (e) determining nucleotide sequences from the fragments by detecting the fragments at the locations; and (f) identifying the nucleotide sequences that are derived from a common source in the plurality of different sources based on the nucleotide sequences from the fragments and the relative distances between the locations on the solid support surface.

This disclosure further provides a method of determining the source for individual sequences in a mixture of sequences from different sources, wherein the method includes the steps of (a) providing a mixture of target nucleic acid polymers from a plurality of different sources; (b) modifying the mixture of target nucleic acid polymers to produce a mixture of modified nucleic acid polymers, wherein the mixture of modified nucleic acid polymers includes a plurality of sequence regions from the different sources; (c) attaching the modified nucleic acid polymers to a solid support surface; (d) producing fragments of the modified nucleic acid polymers that are attached to the solid support surface, wherein fragments from a common source of the plurality of sources are attached to locations that are proximal on the solid support surface; (e) determining nucleotide sequences of the fragments at the locations; and (f) identifying the nucleotide sequences that are derived from a common source in the plurality of different sources based on the nucleotide sequences from the fragments and the relative distances between the locations on the solid support surface.

Also provided is a method of determining the source for individual sequences in a mixture of sequences from different sources, wherein the method includes the steps of (a) providing a mixture of target nucleic acid polymers from a plurality of different sources; (b) adding inserts into the target nucleic acid polymers in the mixture to form a mixture of modified nucleic acid polymers, each polymer including a plurality of internal inserts; (c) attaching the modified nucleic acid polymer to a solid support surface; (d) producing fragments of the modified nucleic acid polymers that are attached to the solid support surface, wherein fragments from a common source of the plurality of sources are attached to locations that are proximal on the solid support surface; (e) determining nucleotide sequences from the fragments by detecting the fragments at the locations; and (f) identifying the nucleotide sequences that are derived from a common source in the plurality of different sources based on the nucleotide sequences from the fragments and the relative distances between the locations on the solid support surface.

DETAILED DESCRIPTION

Figure 1A:
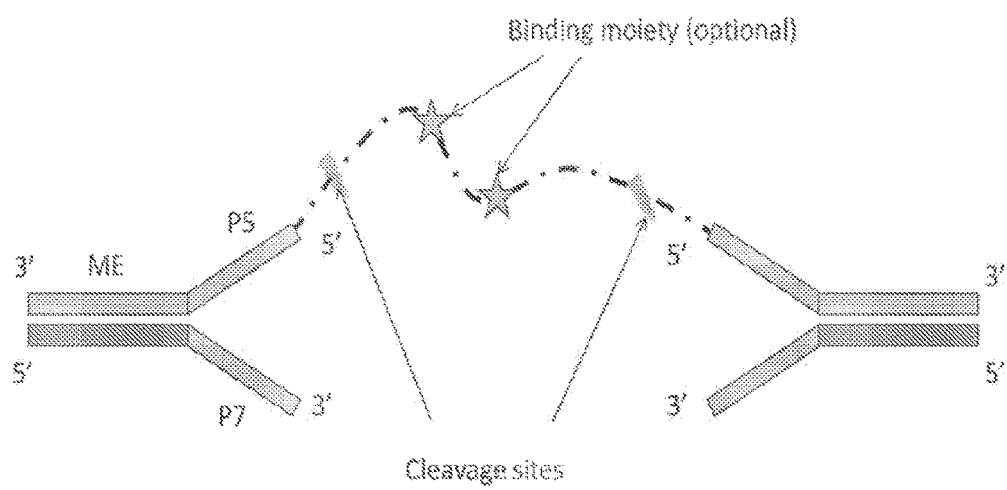
FIG. 1A shows a diagram of an insert having two transposon elements attached via a linker.

Traditional nucleic acid sequencing methods, and so-called next generation sequencing methods, use what is characterized as a shotgun approach. Specifically, genomic DNA, which is packaged by nature into large contiguous polymers called chromosomes, is fragmented into smaller pieces that are amenable to manipulation and detection in sequencing methods. One of the difficulties of this shotgun approach is that by the time the sequences of the individual fragments have been read, knowledge of their connectivity and proximity to each other in the chromosome has been lost. The process of ordering the fragments to arrive at the sequence of the chromosome is generally referred to as "assembly." Assembly processes are generally time consuming and require relatively large computational resources. Sequence and assembly errors can be a problem depending upon the sequencing methodology used and the quality of genomic DNA samples under evaluation.

Moreover, many genomes of interest contain more than one version of each chromosome. For example, the human genome is diploid, having two sets of chromosomes—one set inherited from each parent. Some organisms have polyploid genomes with more than two sets of chromosomes. Examples of polyploid organisms include animals, such as salmon, and many plant species such as wheat, apple, oat and sugar cane. When diploid and polyploid genomes are fragmented and sequenced in typical shotgun methods, phasing information, pertaining to the identity of which fragments came from which set of chromosomes, is lost. This phasing information can be difficult or impossible to reconstruct using typical shotgun methods.

Somewhat similar yet often more complex difficulties can arise when mixed samples are evaluated. Mixed samples can contain nucleic acid molecules, such as chromosomes, mRNA transcripts, plasmids etc., from two or more organisms. Mixed samples having multiple organisms are often referred to as metagenomic samples. Other examples of mixed samples are different cells or tissues that although being derived from the same organism have different characteristics. Examples include cancerous tissues which may comprise a mixture of healthy cells and cancerous cells, tissues that may comprise pre-cancerous cells and cancerous cells, tissue that may comprise two or more different types of cancerous cells. Indeed there may be a variety of different types of cancer cells as is the case for cancer samples that have mosaicity. Another example of different cells derived from a single organism are mixtures of maternal and fetal cells obtained from a pregnant female (e.g. from the blood or from tissues). When mixed nucleic acid samples are fragmented and sequenced in typical shotgun methods information pertaining to the identity of which fragments came from which cell, organism or other source is lost. This origin information can be difficult or impossible to reconstruct using typical shotgun methods.

The present disclosure provides modified versions of target nucleic acids that preserve connectivity information for sequence regions present in the original target nucleic acids from which they were produced. Using methods set forth herein, fragments of the modified nucleic acids can be produced and captured on localized regions of a solid support surface. In cases where mixtures of different modified nucleic acids are used, the fragments produced from each nucleic acid molecule can be localized to respective regions on the surface (albeit that each fragment will randomly end up at a location that is not predefined). As such the proximity of different fragments on the surface can be used to determine which fragments were derived from a common target nucleic acid molecule. This information can in turn be used to determine phasing and haplotyping for fragments derived from longer molecules or to identify two or more fragments that were derived from a common cell, organism or other source.

Methods of the present disclosure can provide benefits of facilitating assembly, improving error correction, identifying nucleic acid origin in mixed samples and determining phasing information. Particular embodiments provide fragments of genomic DNA (or other target nucleic acids) in an arrangement or composition that correlates with proximity of the fragment sequences in a particular chromosome (or other nucleic acid). Sequencing of the fragments and evaluation of their relative locations in the arrangement or composition can be used to facilitate assembly, identify and correct errors in the assembled sequence, and determine phase for haplotypes or other sequence features. Sequence and relative proximity information can also be useful for identifying sequences that were derived from a common source even though the sequences were identified from many fragments obtained from a mixture of sources.

By way of a more specific example, methods are provided to process long target nucleic acid polymers to introduce insert elements that subdivide the polymer into linked sections. The insert elements can provide various capabilities such as priming sites for amplification and/or sequencing processes, ligands for capture to surfaces, and/or cleavage sites for fragmenting the polymer. The polymer having the insert elements can be introduced into a flow cell, or other vessel, having a surface for capture and detection of nucleic acid fragments. Fragments of the polymer can then be produced at or near the surface such that fragments that are from proximal sections of the polymer end up at sites on the surface that are proximal to each other. The fragments can optionally be amplified at the sites and then detected in a sequencing technique. Fragments within a given distance from one another will have a significant probability of having come from the same target nucleic acid polymer and this information can be used to facilitate assembly, error correction, identification of origin in mixed samples and phasing.

As set forth in further detail below, the methods set forth herein can be applied as an improvement to shotgun sequencing approaches such as those commercially recognized as next generation sequencing or set forth in references cited herein.

Terms used herein will be understood to take on their ordinary meaning in the relevant art unless specified otherwise. Several terms used herein and their meanings are set forth below.

As used herein, the term "actively transported" refers to movement of a molecule toward or away from a location due to non-diffusive forces imposed on the molecule. The location can be a location on a solid support surface (e.g. on an array). Non-diffusive forces can be provided by an external source such as those that produce an electrical or magnetic field, fluid flow, or chemical gradient. Actively transported molecules can move along their concentration gradient or against their concentration gradient. Thus, active transport can include applying energy to move one or more molecule in a desired direction or to a desired location on a solid support.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features or locations on the same substrate. Exemplary sites include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "attached" refers to the state of two things being joined, fastened, adhered, connected or bound to each other. For example, an analyte, such as a nucleic acid, can be attached to a material, such as a surface of a solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions. In some embodiments, the attachment occurs via one or more covalent bonds such that the attachment is not mediated by any non-covalent bonds As used herein, the term "cleavage site" is intended to mean a moiety in a molecule, such as a linker, that can be modified or removed to physically separate two other moieties of the molecule. A cleavage site can be susceptible to modification or removal via biochemical, chemical, physical or other means.

As used herein, the term "contiguous," when used in reference to two transposon elements, is intended to mean the two transposon elements are covalently attached to each other via a linker. A linker can attach at or near the 5' ends of the two transposon elements (see FIG. 1 for an example), at or near the 3' ends of the two transposons, or at or near the 3' end of one of the transposons and at or near the 5' end of the other transposon. Examples of contiguous transposon elements that can be useful are described in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more different nucleic acids can have target nucleotide sequence portions that are different from each other while also having a universal sequence region that is the same for the two or more different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extension," when used in reference to a primer is intended to include processes wherein one or more nucleotides are added to the primer (e.g. via polymerase activity) or wherein one or more oligonucleotides are added to the primer (e.g. via ligase activity).

As used herein, the term "flow cell" is intended to mean a chamber having a surface across which one or more fluid reagents can be flowed. Generally, a flow cell will have an ingress opening and an egress opening to facilitate flow of fluid. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

As used herein, the term "forked adapter" is intended to mean a double stranded nucleic acid having a first end wherein the two strands are annealed to each other and a second end wherein the two strands are not annealed to each other. Examples of forked or Y-shaped adapters are described, for example, in U.S. Pat. No. 7,741,463, which is incorporated herein by reference.

As used herein, the term "fragment," when used in reference to a first nucleic acid, is intended to mean a second nucleic acid having a part or portion of the sequence of the first nucleic acid. Generally, the fragment and the first nucleic acid are separate molecules. The fragment can be derived, for example, by physical removal from the larger nucleic acid, by replication or amplification of a region of the larger nucleic acid, by degradation of other portions of the larger nucleic acid, a combination thereof or the like. The term can be used analogously to describe sequence data or other representations of nucleic acids.

As used herein, the term "haplotype" refers to a set of alleles at more than one locus inherited by an individual from one of its parents. A haplotype can include two or more loci from all or part of a chromosome. Alleles include, for example, single nucleotide polymorphisms (SNPs), short tandem repeats (STRs), gene sequences, chromosomal insertions, chromosomal deletions etc. The term "phased alleles" refers to the distribution of the particular alleles from a particular chromosome, or portion thereof. Accordingly, the "phase" of two alleles can refer to a characterization or representation of the relative location of two or more alleles on one or more chromosomes.

As used herein, the term "insert," when used in reference to a polymer is intended to mean a molecule that is, has been or will be attached to the polymer. The polymer can be, for example, a nucleic acid such as DNA, RNA or analog thereof. The molecule can be, for example, a nucleic acid, an analog thereof, or a molecule having a nucleic acid moiety or analog thereof.

As used herein, the term "internal," when used in reference to a polymer having two ends, is intended to mean at a location in the polymer that is between the two ends of the polymer. For example, an insert that is internal to a polymer can be located at a position that is least 1, 2, 3, 4, 5, 10, 100, 200, 500 or 1000 monomer subunits from the end of the polymer.

As used herein, the terms "ligand" and "receptor" are intended to refer to components that specifically bind to each other to form a complex. Examples of ligands and receptors include, but are not limited to, polyhistidine (e.g., penta-His and hexa-His) and nickel; avidin (or analogs thereof such as streptavidin) and biotin (or analogs thereof such as 2-iminobiotin, desthiobiotin, NeutrAvidin (Molecular Probes, Eugene, Oreg.), CaptAvidin (Molecular Probes), and the like); binding proteins and their substrates (e.g. maltose and maltose binding protein (MBP), calcium and calcium binding protein/peptide (CBP); antibody and antigens such as c-MYC, HA, VSV-G, HSV, V5, and FLAG Tag™); aptamers and their corresponding targets; fluorophores and anti-fluorophore antibodies; nucleic acids and their complements; and the like. For purposes of the present disclosure the terms "ligand" and "receptor" can be used interchangeably unless context or explicit disclosure indicates otherwise. Thus, for example, an antibody may be considered a receptor or a ligand relative to an antigen.

As used herein, the term "linker" is intended to mean a chemical bond or moiety that covalently bridges two other moieties. A linker can be, for example, the sugar-phosphate backbone that connects nucleotides in a nucleic acid moiety. The linker can include, for example, one or more of a nucleotide moiety, a nucleic acid moiety, a non-nucleotide chemical moiety, a nucleotide analogue moiety, amino acid moiety, polypeptide moiety, or protein moiety. A linker can be non-amplifiable, for example, by virtue of containing a non-nucleic acid moiety. Exemplary linkers are set forth in further detail below and in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference.

As used herein the term "nucleic acid" can refer to at least two nucleotide monomers linked together. Examples include, but are not limited to DNA, such as genomic or cDNA; RNA, such as mRNA, sRNA or rRNA; or a hybrid of DNA and RNA. As apparent from the examples below and elsewhere herein, a nucleic acid can have a naturally occurring nucleic acid structure or a non-naturally occurring nucleic acid analog structure. A nucleic acid can contain phosphodiester bonds; however, in some embodiments, nucleic acids may have other types of backbones, comprising, for example, phosphoramide, phosphorothioate, phosphorodithioate, O-methylphosphoroamidite and peptide nucleic acid backbones and linkages. Nucleic acids can have positive backbones; non-ionic backbones, and non-ribose based backbones. Nucleic acids may also contain one or more carbocyclic sugars. The nucleic acids used in methods or compositions herein may be single stranded or, alternatively double stranded, as specified. In some embodiments a nucleic acid can contain portions of both double stranded and single stranded sequence, for example, as demonstrated by forked adapters. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc. In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

As used herein, the term "nucleotide sequence" is intended to refer to the order and type of nucleotide monomers in a nucleic acid polymer. A nucleotide sequence is a characteristic of a nucleic acid molecule and can be represented in any of a variety of formats including, for example, a depiction, image, electronic medium, series of symbols, series of numbers, series of letters, series of colors, etc. The information can be represented, for example, at single nucleotide resolution, at higher resolution (e.g. indicating molecular structure for nucleotide subunits) or at lower resolution (e.g. indicating chromosomal regions, such as haplotype blocks). A series of "A," "T," "G," and "C" letters is a well-known sequence representation for DNA that can be correlated, at single nucleotide resolution, with the actual sequence of a DNA molecule. A similar representation is used for RNA except that "T" is replaced with "U" in the series.

As used herein, the term "passively diffuse" is intended to mean movement of molecules along their concentration gradient.

As used herein, the term "random" can be used to refer to the spatial arrangement or composition of locations on a surface. For example, there are at least two types of order for an array described herein, the first relating to the spacing and relative location of features (also called "sites") and the second relating to identity or predetermined knowledge of the particular species of molecule that is present at a particular feature. Accordingly, features of an array can be randomly located such that nearest neighbor features have random spacing between each other. Alternatively, the spacing between features can be ordered, for example, forming a regular pattern such as a rectilinear grid or hexagonal grid. In another respect, features of an array can be random with respect to the identity or predetermined knowledge of the species of analyte (e.g. nucleic acid of a particular sequence) that occupies each feature independent of whether spacing produces a random pattern or regular pattern. An array set forth herein can be ordered in one respect and random in another. For example, in some embodiments set forth herein a surface is contacted with a population of nucleic acids under conditions where the nucleic acids attach at sites that are ordered with respect to their relative locations but random with respect to knowledge of the sequence for the nucleic acid species present at any particular site. Reference to "randomly" capturing different nucleic acids at locations on a surface is intended to refer to the absence of knowledge or absence of predetermination regarding which nucleic acid will be captured at which location (regardless of whether the locations are arranged in an ordered pattern or not).

As used herein, the term "region," when used in reference to a surface, means an area of the surface that is smaller than the entire area of the surface. The regions can be an area that is smaller than the entire area of a surface that is exposed or accessible to a fluid. Generally the term "region" is used to refer to a continuous, uninterrupted area of a surface, whether or not the region encompasses surface features, sites, contours etc. A region can encompass one or more locations to which a nucleic acid is attached or will be attached.

As used herein, the term "single species" is intended to refer to substantially one and only one species of a particular genera. The term is not necessarily intended to limit the number of representatives of a single species that are present. For example, a population of nucleic acid molecules, each molecule having the same nucleotide sequence, comprise a single species of nucleic acid. The term "single" in this context is not intended to exclude the presence of other things that are not within the relevant genera. For example, a location on a surface that contains a single species of nucleic acid from a library can include multiple nucleic acids having the same sequence, will exclude other target nucleic acids from the library, but need not necessarily exclude any other non-nucleic acid components. It will be understood that an apparent single species population can have a small amount of another species present at a level that is considered by those skilled in the art to be a negligible level of contamination or artifact for the particular use of the population. For example, a nucleic acid cluster, derived from a single template having a first sequence, will be considered to have an apparent single species if the amount of any nucleic acid molecules having a second sequence is sufficiently low to be undetectable or ignored when the first sequence is detected. Alternatively, an absolute single species population will have one and only one species.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus. Exemplary flow cells are set forth in further detail below.

As used herein, the term "source" is intended to include an origin for a nucleic acid molecule, such as a tissue, cell, organelle, compartment, or organism. The term can be used to identify or distinguish an origin for a particular nucleic acid in a mixture that includes origins for several other nucleic acids. A source can be a particular organism in a metagenomic sample having several different species of organisms. In some embodiments the source will be identified as an individual origin (e.g. an individual cell or organism). Alternatively, the source can be identified as a species that encompasses several individuals of the same type in a sample (e.g. a species of bacteria or other organism in a metagenomic sample having several individual members of the species along with members of other species as well).

As used herein, the term "surface," when used in reference to a material, is intended to mean an external part or external layer of the material. The surface can be in contact with another material such as a gas, liquid, gel, polymer, organic polymer, second surface of a similar or different material, metal, or coat. The surface, or regions thereof, can be substantially flat. The surface can have surface features such as wells, pits, channels, ridges, raised regions, pegs, posts or the like. The material can be, for example, a solid support, gel, or the like.

As used herein, the term "target," when used in reference to a nucleic acid polymer, is intended to linguistically distinguish the nucleic acid, for example, from other nucleic acids, modified forms of the nucleic acid, fragments of the nucleic acid, and the like. Any of a variety of nucleic acids set forth herein can be identified as target nucleic acids, examples of which include genomic DNA (gDNA), messenger RNA (mRNA), copy DNA (cDNA), and derivatives or analogs of these nucleic acids.

As used herein, the term "transposase" is intended to mean an enzyme that is capable of forming a functional complex with a transposon element-containing composition (e.g., transposons, transposon ends, transposon end compositions) and catalyzing insertion or transposition of the transposon element-containing composition into a target DNA with which it is incubated, for example, in an in vitro transposition reaction. The term can also include integrases from retrotransposons and retroviruses. Transposases, transposomes and transposome complexes are generally known to those of skill in the art, as exemplified by the disclosure of US Pat. App. Pub. No. 2010/0120098, which is incorporated herein by reference. Although many embodiments described herein refer to Tn5 transposase and/or hyperactive Tn5 transposase, it will be appreciated that any transposition system that is capable of inserting a transposon element with sufficient efficiency to tag a target nucleic acid can be used. In particular embodiments, a preferred transposition system is capable of inserting the transposon element in a random or in an almost random manner to tag the target nucleic acid.

As used herein, the term "transposome" is intended to mean a transposase enzyme bound to a nucleic acid. Typically the nucleic acid is double stranded. For example, the complex can be the product of incubating a transposase enzyme with double-stranded transposon DNA under conditions that support non-covalent complex formation. Transposon DNA can include, without limitation, Tn5 DNA, a portion of Tn5 DNA, a transposon element composition, a mixture of transposon element compositions or other nucleic acids capable of interacting with a transposase such as the hyperactive Tn5 transposase.

As used herein, the term "transposon element" is intended to mean a nucleic acid molecule, or portion thereof, that includes the nucleotide sequences that form a transposome with a transposase or integrase enzyme. Typically, the nucleic acid molecule is a double stranded DNA molecule. In some embodiments, a transposon element is capable of forming a functional complex with the transposase in a transposition reaction. As non-limiting examples, transposon elements can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US Pat. App. Pub. No. 2010/0120098, which is incorporated herein by reference. Transposon elements can comprise any nucleic acid or nucleic acid analogue suitable for forming a functional complex with the transposase or integrase enzyme in an in vitro transposition reaction. For example, the transposon end can comprise DNA, RNA, modified bases, non-natural bases, modified backbone, and can comprise nicks in one or both strands.

As used herein, the term "universal sequence" refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication, amplification, or sequence analysis of multiple different nucleic acids using a population of universal primers that are complementary to the universal sequence. Thus a universal capture nucleic acid or a universal primer includes a sequence that can hybridize specifically to a universal sequence.

The embodiments set forth below and recited in the claims can be understood in view of the above definitions.

The present disclosure provides a method of sequencing a target nucleic acid polymer. The method can include the steps of (a) modifying a target nucleic acid polymer to produce a modified nucleic acid polymer, wherein the modified nucleic acid polymer includes a plurality of sequence regions from the target nucleic acid polymer; (b) producing fragments of the modified nucleic acid polymer in a vessel having a solid support surface, each fragment comprising one of the sequence regions; (c) capturing the fragments randomly at locations in a region of the solid support surface; (d) determining nucleotide sequences of the sequence regions by detecting the fragments at the locations; and (e) producing a representation of the nucleotide sequence for the target nucleic acid polymer based on the nucleotide sequences from the fragments and the relative distances between the locations on the solid support surface.

This disclosure further provides a method of sequencing a target nucleic acid polymer, that includes the steps of (a) modifying a target nucleic acid polymer to produce a modified nucleic acid polymer, wherein the modified nucleic acid polymer includes a plurality of sequence regions from the target nucleic acid polymer; (b) attaching the modified nucleic acid polymer to a region on a solid support surface; (c) producing fragments of the modified nucleic acid polymer that is attached to the solid support surface, wherein the fragments are attached to locations at the region of the solid support surface; (d) determining nucleotide sequences from the fragments by detecting the fragments at the locations; and (e) producing a representation of the nucleotide sequence for the target nucleic acid polymers based on the nucleotide sequences from the fragments and the relative distances between the locations on the solid support surface.

The present disclosure provides a method of determining the source for individual sequences in a mixture of sequences from different sources. The method can include the steps of (a) providing a mixture of target nucleic acid polymers from a plurality of different sources; (b) modifying the mixture of target nucleic acid polymers to produce a mixture of modified nucleic acid polymers, wherein the mixture of modified nucleic acid polymers includes a plurality of sequence regions from the different sources; (c) producing fragments of the modified nucleic acid polymers in a vessel having a solid support surface, each fragment comprising a sequence region from a single one of the different sources; (d) capturing the fragments randomly at locations of the solid support surface, under conditions wherein fragments from a common target nucleic acid polymer preferentially localize to proximal locations on the solid support surface; (e) determining nucleotide sequences of the fragments at the locations; and (f) identifying the nucleotide sequences that are derived from a common source in the plurality of different sources based on the nucleotide sequences from the fragments and the relative distances between the locations on the solid support surface.

Also provided is a method of determining the source for individual sequences in a mixture of sequences from different sources, wherein the method includes the steps of (a) providing a mixture of target nucleic acid polymers from a plurality of different sources; (b) adding inserts into the target nucleic acid polymers in the mixture to form a mixture of modified nucleic acid polymers, each polymer including a plurality of internal inserts; (c) producing fragments of the modified nucleic acid polymers in a fluid that is in contact with a solid support surface, thereby releasing fragments that each include at least a portion of each of the inserts; (d) capturing the fragments from the fluid randomly at locations on a solid support surface; (e) determining nucleotide sequences from the fragments by detecting the fragments at the locations; and (f) identifying the nucleotide sequences that are derived from a common source in the plurality of different sources based on the nucleotide sequences from the fragments and the relative distances between the locations on the solid support surface.

A target nucleic acid that is useful in a method or composition herein can have a structure and/or origin as set forth elsewhere herein. Exemplary nucleic acid species that can be targets herein include, but are not limited to DNA, RNA, peptide nucleic acid, morpholino nucleic acid, locked nucleic acid, glycol nucleic acid, threose nucleic acid, mixtures thereof, and hybrids thereof. In a preferred embodiment, genomic DNA fragments, or amplified copies thereof, are used as the target nucleic acid. In another preferred embodiment, mitochondrial or chloroplast DNA is used. Still other embodiments are targeted to RNA or derivatives thereof such as mRNA or cDNA. IN some embodiments, target nucleic acid can be from a single cell. In some embodiments, target nucleic acid can be from acellular body fluids, for example, plasma or sputum devoid of cells. In some embodiments, target nucleic acid can be from circulating tumor cells.

In some embodiments, the target nucleic acid can include ribosomal RNA (rRNA) or sequences derived therefrom. For example, rRNA sequences can be particularly useful for distinguishing different organisms in a metagenomic sample.

A target nucleic acid can have any of a variety of nucleotide sequences. In some embodiments, the target nucleic acid includes homopolymer sequences. A target nucleic acid can also include repeat sequences. The repeat unit can be, for example, at least 2, 5, 10, 20, 30, 40, 50, 100, 250, 500, 1000 nucleotides or more. Repeat sequences can be repeated, either contiguously or non-contiguously, any of a variety of times including, for example, at least 2, 3, 4, 5, 6, 7, 8, 9, 10, 15, 20 times or more. The methods set forth herein are particularly useful for analyzing and evaluating target nucleic acids having homopolymer and/or repeat sequences because the true length of these sequence regions can be determined from sequence assemblies that are derived, at least in part from proximity information obtained from the methods.

Some embodiments described herein can utilize a single target nucleic acid species, present in one copy (i.e. single molecule) or, alternatively present in multiple copies (i.e. an ensemble of nucleic acid molecules having the same sequence). Other embodiments can utilize a plurality of different target nucleic acid species (i.e. nucleic acid molecules having different nucleotide species being present in the plurality). Thus, a plurality of target nucleic acids can include a plurality of the same target nucleic acids, a plurality of different target nucleic acids where some target nucleic acids are the same, or a plurality of target nucleic acids where all target nucleic acids are different.

Embodiments that utilize a plurality of target nucleic acids can be carried out in multiplex formats such that reagents are delivered simultaneously to the target nucleic acids in the plurality or the target nucleic acids in the plurality are manipulated simultaneously (e.g. one or more steps of the methods set forth herein can be carried out simultaneously on the target nucleic acids that are in the plurality). Target nucleic acids, or derivatives of the target nucleic acids (e.g. fragments and/or amplicons) can be provided in one or more chambers or on an array surface for convenient multiplex manipulation and/or evaluation.

In some embodiments, a plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome. Exemplary genomes from which target nucleic acids can be obtained include, without limitation prokaryotes (e.g. *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, and Streptomyces* genera); *Achaea*, such as *crenarchaeota, nanoarchaeota* or *euryarchaeotia*; or eukaryotes such as fungi, (for example, yeasts), plants, protozoans, and animals (including insects (for example, *Drosophila* spp.), nematodes (e.g., *Caenorhabditis elegans*), and mammals (for example, rat, mouse, monkey, non-human primate and human)).

A plurality of target nucleic acids can have a complexity that is equivalent to at least about 3 Gigabases, which is the size of the haploid human genome, at least about 2 Gigabases, which is a representation of at least about 60% of the human genome or at least about 1 Gigabases, which is a representation of at least about 30% of the human genome. The complexity of a plurality of target nucleic acid can be larger or smaller than the human genome being, for example, at least about 0.1 Gigabases, 0.2 Gigabases, 0.5 Gigabases, 0.8 Gigabases, 1 Gigabases, 1.5 Gigabases, 2 Gigabases, 2.5 Gigabases, 3 Gigabases, 3.5 Gigabases, 4 Gigabases, 4.5 Gigabases, 5 Gigabases or more. Alternatively or additionally, the complexity or a plurality of nucleic acids used in an embodiment herein can be no more than about 5 Gigabases, 4 Gigabases, 3 Gigabases, 2 Gigabases, 1 Gigabases, 0.5 Gigabases, 0.1 Gigabases or less.

In some embodiments a plurality of target nucleic acids include RNA from a desired organism, examples of which include, but are not limited to those set forth above. A target nucleic acid sample can include substantially all or part of the complete complement of RNA present in the organism. The plurality of target nucleic acids can include at least a portion of a particular organism's transcriptome including, for example, at least about 1%, 5%, 10%, 25%, 50%, 75%, 80%, 85%, 90%, 95%, or 99% of the transcriptome. Alternatively or additionally, the portion can have an upper limit that is at most about 1%, 5%, 10%, 25%, 50%, 75%, 80%, 85%, 90%, 95%, or 99% of the transcriptome.

In some embodiments, a target nucleic acid or modified nucleic acid that is produced by integration of an insert into the target nucleic acid can be at least 0.1 kb, 1 kb, 2 kb, 3 kb, 4 kb, 5 kb, 6 kb, 7 kb, 8 kb, 9 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1000 kb, 5000 kb, 10000 kb, 20000 kb, 30000 kb, or at least 50000 kb in length. Alternatively or additionally, the target nucleic acid or modified nucleic acid is no more than 0.1 kb, 1kb, 2 kb, 3 kb, 4 kb, 5 kb, 6 kb, 7 kb, 8 kb, 9 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, or no more than 1000 kb in length.

Target nucleic acids may be prepared from nucleic acid molecules obtained from a single organism or from populations of nucleic acid molecules obtained from natural sources that include more than one organism. A target nucleic acid can be from a single cell; from multiple cells, tissue(s) or bodily fluids of a single organism; from cells, tissues or bodily fluids of several organisms of the same species; or from multiple species, as with metagenomic samples, such as from environmental samples. Sources of nucleic acid molecules include, but are not limited to, organelles, cells, tissues, organs, or organisms.

A target nucleic acid sample can, in some embodiments, be processed prior to adding inserts or prior to performing other modifications set forth herein. For example, a target nucleic acid sample can be amplified prior to adding inserts, prior to attaching to a bead, prior to attaching to the surface of a solid support, or prior to binding to transposases. Amplification is particularly useful when samples are in low abundance or when small amounts of a target nucleic acid are provided. Methods that amplify the vast majority of sequences in a genome are referred to as "whole genome amplification" methods. Examples of such methods include multiple displacement amplification (MDA), strand displacement amplification (SDA), or hyperbranched strand displacement amplification, each of which can be carried out using degenerate primers. Particularly useful methods are those that are used during sample preparation methods recommended by commercial providers of whole genome sequencing platforms (e.g. Illumina Inc., San Diego and Life Technologies Inc., Carlsbad). Other useful methods are set forth in U.S. Pat. No. 7,670,810, which is incorporated herein by reference.

Targeted amplification can be used to selectively amplify only a portion of a nucleic acid whether it is a target nucleic acid, modified nucleic acid, nucleic acid fragment or other nucleic acid set forth herein. Examples of targeted amplification techniques include, but are not limited to multiplex PCR, GoldenGate assay (Illumina Inc., San Diego), rolling circle amplification and other methods known in the art such as those described in U.S. Pat. No. 7,670,810; U.S. Pat. No. 6,355,431 or U.S. Pat. No. 7,582,420, each of which is incorporated herein by reference. Other useful methods for selective enrichment and, optionally amplification, of targeted regions of a genome include targeted probe pullout techniques such as those commercialized by Illumina Inc. under the TruSeq™ brand, by NimbleGen Inc. under the SeqCap EZ™ brand or by Agilent, Inc. under the SureSelect™ brand.

A target nucleic acid sample can, in some embodiments, be fragmented prior to adding inserts or prior to performing other modifications set forth herein. In some embodiments, fragmentation inherently results from amplification, for example, in cases where the portion of the template that occurs between sites where flanking primers hybridize is selectively copied. In other cases fragmentation can be achieved using chemical, enzymatic or physical techniques known in the art. Fragments in a desired size range can be obtained using separation methods known in the art such as gel electrophoresis or purification using SPRI® beads (AgenCourt, Beverly Mass.). Accordingly, fragmentation can be carried out to obtain target DNA polymers, prior to insert addition, that are at most about 10 kb, 5 kb, 4 kb, 3 kb, 2 kb, 1 kb, 0.8 kb, 0.6 kb, 0.5 kb, 0.4 kb, 0.2 kb, or 0.1 kb or shorter in length. Alternatively or additionally, size selection can be used to obtain target nucleic acid polymers having a maximum size selected from those exemplified above and a minimum size of at least about 0.1 kb, 0.5 kb, 1 kb, 2 kb, 3, kb, 4 kb, 5 kb, 10 kb or longer in length.

A method of the present disclosure can include a step of modifying a target nucleic acid polymer to produce a modified nucleic acid polymer, wherein the modified nucleic acid polymer includes a plurality of sequence regions from the target nucleic acid polymer. Exemplary modifications include, but are not limited to, binding transposase enzymes to the target nucleic acids to form transposomes, adding inserts into the target nucleic acids, attaching the target nucleic acids to a bead or other carrier, or attaching the target nucleic acids to the surface of a substrate where fragments will subsequently be captured.

In particular embodiments a target nucleic acid polymer can be modified by adding one or more inserts into the polymer. Thus, a method of the present disclosure can include a step of adding an insert into a target nucleic acid polymer, thereby preparing a modified nucleic acid. Some methods of insertion include contacting an insert, having a transposon element, with a target nucleic acid in the presence of an enzyme, such as a transposase or integrase, under conditions sufficient for the integration of the insert into the target nucleic acid. In some embodiments, addition of the insert into a target nucleic acid can be non-random. In some embodiments, inserts having transposon elements can be contacted with target nucleic acids in the presence of one or more proteins that inhibit integration at certain sites. For example, inserts can be inhibited from integrating into genomic DNA comprising proteins, genomic DNA comprising chromatin, genomic DNA comprising nucleosomes, or genomic DNA comprising histones.

Figure 5:
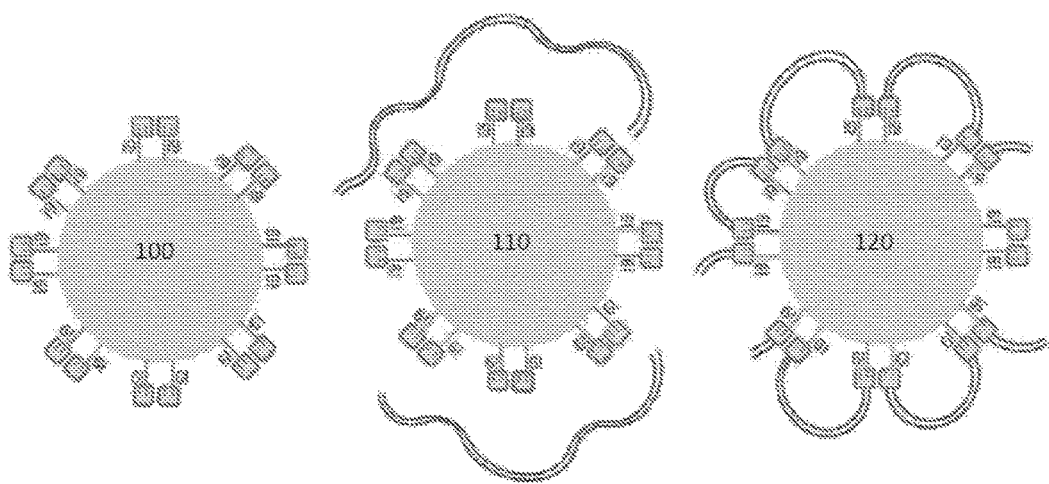
FIG. 5 shows attachment of target nucleic acids to a bead followed by fragmentation of the target nucleic acid on the bead.

A step of adding inserts to a target nucleic acid can be carried out for a target nucleic acid that is in solution, for example, as diagramed in FIG. 1. As set forth in further detail below the solution-phase target nucleic acid can be used to produce fragments that will subsequently bind to the surface of a solid support. In an alternative embodiment, a target nucleic acid can be captured on a bead or other solid-phase carrier such that inserts are added to the target nucleic acid while it is attached to the solid-phase carrier. FIG. 5 shows a bead 100 having attached transposases, a similar bead 110 in the presence of a solution-phase target nucleic acids and a bead 120 where target nucleic acids have bound to the transposases on the surface of the bead. The target nucleic acids can be tagmented on the surface of the bead. A solid-phase carrier can be made from a solid support material (i.e. being rigid) or from other insoluble materials whether or not the materials are rigid or compressible (e.g. hydrogel beads).

Figure 6:
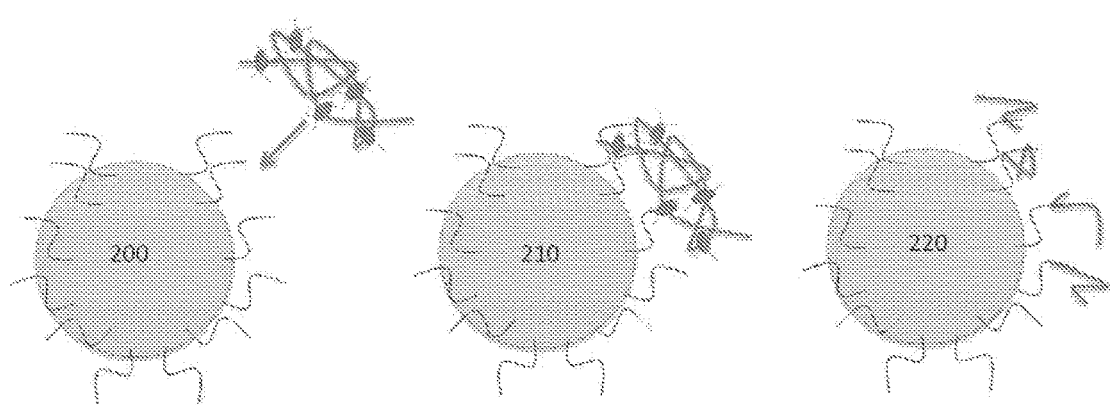
FIG. 6 shows attachment of a modified nucleic acid to a bead followed by fragmentation of the target nucleic acid on the bead.

Another embodiment that can be used to add inserts into target nucleic acid on solid-phase is shown in FIG. 6. In this example, bead 200 has attached nucleic acid probes that are complementary to inserts added into a modified nucleic acid. The inserts have been added into the modified nucleic acid by transposases and the modified nucleic acid is bound to bead 210 by annealing of the probes to the inserts to form a solid-phase, modified nucleic acid. Transposomes can be present on the modified nucleic acid when it is bound to the bead (as shown in FIG. 6) or the transposomes can be removed prior to this binding. The solid-phase, modified nucleic acid can be fragmented on the bead to produce bead 220 having solid-phase, nucleic acid fragments.

Any of a variety of target nucleic acids or modified nucleic acids set forth herein can be attached to a bead or other solid phase carrier. Accordingly, steps set forth herein for making and using a target nucleic acid, modified nucleic acid or nucleic acid fragment can be carried out before or after solid-phase attachment. For example, a target nucleic acid can be attached to a bead or other solid-phase carrier and then the attached target nucleic acid can be treated with a transposase, integrase or other reagent that introduces inserts. Furthermore, inserts need not be added to solid-phase target nucleic acids and instead the solid-phase target nucleic acids can be fragmented without addition of inserts. A bead or other solid-phase carrier that is bound to a target nucleic acid, modified nucleic acid or fragments thereof can be delivered to a vessel having a surface where nucleic acid fragments will be sequenced or otherwise detected.

Figure 7:
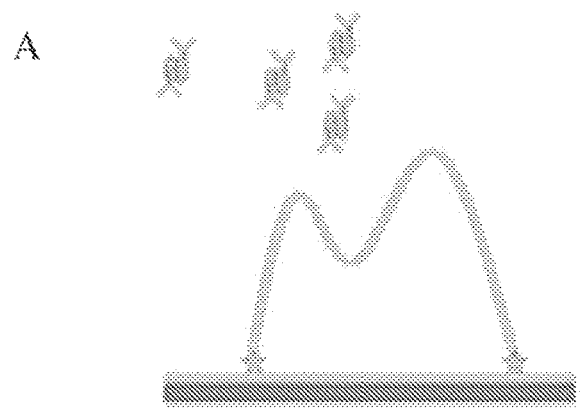
FIG. 7 shows modification of a target nucleic acid on a solid support surface and release of fragments from the surface into solution.
Figure 7:
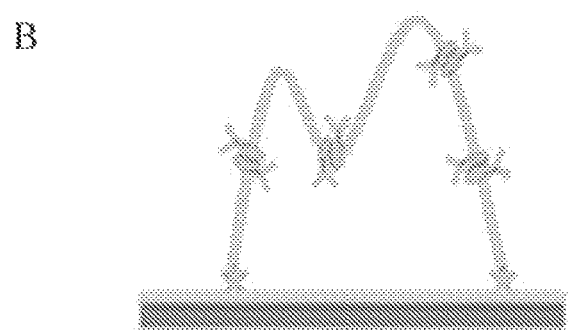
Figure 7:
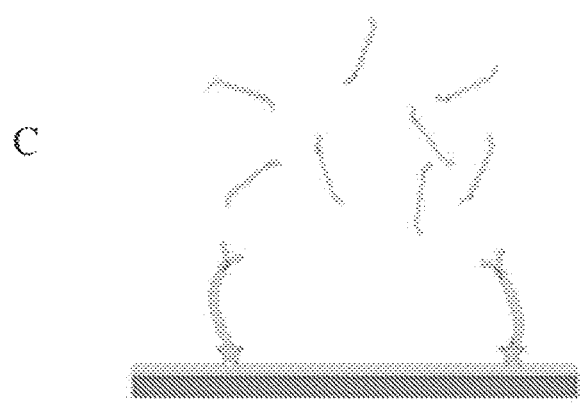

A further example of adding inserts to a solid-phase target nucleic acid is shown in FIG. 7. As shown in Panel A, a target nucleic acid is attached to a surface via linkages at or near the ends of the target nucleic acid. If desired, attachment can occur at other points on the target nucleic acid. In panel B, transposases are bound to the solid-phase target nucleic acid to form multiple solid-phase transposomes. The target nucleic acid can be tagmented such that multiple different fragments are released from the surface as shown in Panel C. The released fragments can then be recaptured on a region of the surface that is proximal to the site where the target nucleic acid had been captured. The captured fragments can be further manipulated and detected using methods set forth herein.

Whether using solution-phase or solid-phase target nucleic acids, inserts can have any of a variety of moieties or portions. In particular embodiments, inserts can be associated with affinity tags in order to integrate a transposon element of the insert at a particular sequence in a target nucleic acid. For example, an insert may be associated with a protein that targets specific nucleic acid sequences, e.g., histones, chromatin-binding proteins, transcription factors, initiation factors, etc., and antibodies or antibody fragments that bind to particular sequence-specific nucleic-acid-binding proteins. In an exemplary embodiment, an insert is associated with an affinity tag, such as biotin; and the affinity tag is associated with a nucleic-acid-binding protein.

It will be understood that during integration of some inserts that bear transposon elements, several consecutive nucleotides at the integration site of the target nucleic acid are duplicated in the integrated product. Thus the integrated product can include a duplicated sequence at each end of the insert region in the resulting modified nucleic acid, for example as described in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference. The duplicated sequence can be used as a host tag. For example, Tn5 transposases bind target nucleic acids and generate two nicks in the DNA backbone, 9 bases apart on either strand. The 9 base region provides a host tag that will be present in adjacent fragments. This tag can be used to confirm that fragments which are proximal on a surface and which also have the same tag sequence did indeed come from the same target nucleic acid. Thus, the tag can be used for error checking, facilitating assembly of fragment sequences or determining haplotype phase.

In some embodiments, a plurality of the inserts provided herein is added into a particular target nucleic acid polymer. Some embodiments include selecting conditions sufficient to achieve integration of a plurality of transposon sequences into a target nucleic acid polymer such that the average distance between each integrated transposon sequence in the polymer is a certain number of consecutive nucleotides in the target nucleic acid. In some embodiments, conditions may be selected so that the distance or average distance in a target nucleic acid between inserts is at least about 5, 10, 20, 30, 40, 50, 60, 70, 80, 90, 100, or more consecutive nucleotides. In some embodiments, the distance or average distance in a target nucleic acid between inserts is at least about 100, 200, 300, 400, 500, 600, 700, 800, 900, 1000, or more consecutive nucleotides. In some embodiments, the distance or average distance in a target nucleic acid between inserts is at least about 1 kb, 2 kb, 3 kb, 4 kb, 5 kb, 6 kb, 7 kb, 8 kb, 90 kb, 100 kb, or more consecutive nucleotides. In some embodiments, the distance or average distance in a target nucleic acid between inserts is at least about 100 kb, 200 kb, 300 kb, 400 kb, 500 kb, 600 kb, 700 kb, 800 kb, 900 kb, 1000 kb, or more consecutive nucleotides. Alternatively or additionally to the threshold values set forth above, the distance or average distance in a target nucleic acid between inserts can be at most about 1000 kb, 500 kb, 100 kb, 10 kb, 5 kb, 1 kb, 500 bases, 100 bases, 50 bases or 10 bases.

Some embodiments can include copying all or part of the sequences in a nucleic acid. For example, some embodiments include hybridizing a primer to a priming site of an insert integrated into a modified nucleic acid, or fragment thereof. In some such embodiments, the primer can be hybridized to the priming site and extended. The copied sequences can include at least a portion of the target nucleic acid, or fragment thereof. In some embodiments, the primer can be a sequencing primer. In some embodiments sequencing data is obtained using the sequencing primer. Some embodiments of methods set forth herein can include amplifying sequences that include at least a portion of one or more inserts and at least a portion of a target nucleic acid, or fragment thereof. In some embodiments, at least a portion of a target nucleic acid (or fragment thereof) can be amplified using primers that hybridize to priming sites of inserts integrated into a target nucleic acid polymer.

In particular embodiments, inserts are added into a target nucleic acid polymer by transposases. A transposase can form a functional complex with an insert that includes a transposon element thereby forming a transposome. A transposome formed in this way is capable of catalyzing a transposition reaction to integrate the insert into a target nucleic acid polymer. In some such insertion events, one strand of the transposase recognition site may be transferred into the target nucleic acid.

Some embodiments can include the use of a hyperactive Tn5 transposase and a Tn5-type transposase element (see, for example, Goryshin and Reznikoff, *J. Biol. Chem.*, 273: 7367 (1998), which is incorporated herein by reference), or MuA transposase and a Mu transposase element comprising R1 and R2 end sequences (see, for example, Mizuuchi, *Cell*, 35: 785, (1983) and Savilahti, et al., *EMBO J.*, 14: 4893, (1995), each of which is incorporated herein by reference). Exemplary transposase elements that form a complex with a hyperactive Tn5 transposase (e.g., EZ-Tn5™ Transposase, Epicentre Biotechnologies, Madison, Wis.) are set forth in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference.

More examples of transposition systems that can be used with certain embodiments provided herein include *Staphylococcus aureus* Tn552 (Colegio et al., *J. Bacteriol.*, 183: 2384-8 (2001); Kirby et al., *Mol. Microbiol.*, 43: 173-86 (2002)), Ty1 (Devine & Boeke, *Nucleic Acids Res.*, 22: 3765-72 (1994) and PCT Pub. No. WO 95/23875), Transposon Tn7 (Craig, *Science* 271: 1512 (1996); Craig, *Curr Top Microbiol Immunol.*, 204:27-48 (1996)), Tn/O and IS10 (Kleckner et al., *Curr Top Microbiol Immunol.*, 204:49-82 (1996)), Mariner transposase (Lampe et al., *EMBO J.*, 15: 5470-9, (1996)), Tc1 (Plasterk, *Curr. Topics Microbiol. Immunol.*, 204: 125-43, (1996)), P Element (Gloor, *Methods Mol. Biol.*, 260: 97-114, (2004)), Tn3 (Ichikawa & Ohtsubo, *J Biol. Chem.* 265:18829-32, (1990)), bacterial insertion sequences (Ohtsubo & Sekine, *Curr. Top. Microbiol. Immunol.* 204: 1-26, (1996)), retroviruses (Brown, et al., *Proc Natl Acad Sci USA,* 86:2525-9, (1989)), and retrotransposon of yeast (Boeke & Corces, *Annu Rev Microbiol.* 43:403-34, (1989)). More examples include IS5, Tn10, Tn903, IS911, and engineered versions of transposase family enzymes (Zhang et al., *PLoS Genet.* 5:e1000689. Epub 2009 Oct. 16; and Wilson et al *J. Microbiol. Methods* 71:332-5 (2007)). The references cited in this paragraph are each incorporated herein by reference.

Some embodiments provided herein include inserts having transposon elements, modified nucleic acid polymers having transposon elements or nucleic acid fragments having transposon elements. In some embodiments, a transposon element is present in an insert along with other moieties set forth herein such as a linker to a second transposon element, a priming site for amplification, a priming site for primer extension-based detection (e.g. SBS detection), a binding moiety and/or a cleavage site. FIG. 1 depicts a schematic of an insert including a transposon element along with other moieties.

A transposon element can include two nucleic acid strands that comprise a specific binding site for a transposase or integrase. The strands can be fully complementary along their length (e.g., a double-stranded nucleic acid) or complementary along at least a portion of their length (e.g. a forked adapter, adapter with non-complementary overhangs, etc.). An exemplary embodiment of a double stranded transposon element that has complementary strands in an annealed portion and non-complementary strands that form a non-annealed portion is depicted in FIG. 1.

In particular embodiments, an insert includes two transposon elements that are linked to each other. A linker can be included in the insert such that a first transposon element is contiguous with a second transposon element. A particularly useful insert is one that forms a "looped" complex as set forth in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference. In such structures a single insert having contiguous transposon elements binds to two transposase subunits forming a "looped" complex. The looped complex can be used to place the insert into a target nucleic acid while maintaining ordering information of the original target nucleic acid and without fragmenting the resulting modified nucleic acid polymer. Insertion of a looped transposon element provides for adding inserts into a target nucleic acid without necessarily fragmenting the target nucleic acid. As will be set forth in further detail below the resulting modified nucleic acid polymer can be fragmented in a subsequent step.

Useful linkers can have moieties that include, but are not limited to, one or more nucleotide, nucleic acid, non-nucleotide containing chemical moiety, nucleotide analogue, amino acid, polypeptide, or protein. In preferred embodiments, a linker comprises a nucleic acid moiety. The linker can include at least about 1, 2, 3, 4, 5, 6, 7, 8, 9, 10, 11, 12, 13, 14, 15, 16, 17, 18, 19, 20, or more nucleotides. Alternatively or additionally, a linker can include at most about 100, 50, 20, 10, 9, 8, 7, 6, 5, 4, 3, 2 or 1 nucleotide(s). In a preferred embodiment, the linker is single stranded between the double stranded ME ends, for example, to prevent self-insertion.

A linker can be non-amplifiable, for example, by virtue of containing one or more non-nucleic acid moiety. In some cases the linker will not include any nucleic acid material, being completely devoid of nucleotides. Examples of non-amplifiable linkers include synthetic linkers such as those having moieties selected from alkyl, propyl, PEG; non-natural bases such as IsoC, isoG; or any group that does not amplify in DNA-based amplification schemes. For example, transposons containing isoC, isoG pairs can be amplified with dNTP mixtures lacking a complementary isoG and isoC, ensuring that no amplification occurs across the inserted transposons.

In particular embodiments, non-amplifiable linkers can be introduced between Mosaic end (ME) regions. For example, an insert can have the following configuration: ME-priming site-linker-priming site-ME. The priming sites can be the same or different. For example as shown in the construct exemplified in FIG. 1, the priming sites can both be P5 priming sites. It will be understood however, that the construct of FIG. 1 can be modified such that the two P7 priming sites are attached via the linker or such that the P5 priming site on one of the forked adapters is attached to the P7 priming site on the other forked adapter. P5 and P7 priming sites are described in U.S. Pat. No. 8,563,477, which is incorporated herein by reference.

Figure 8:
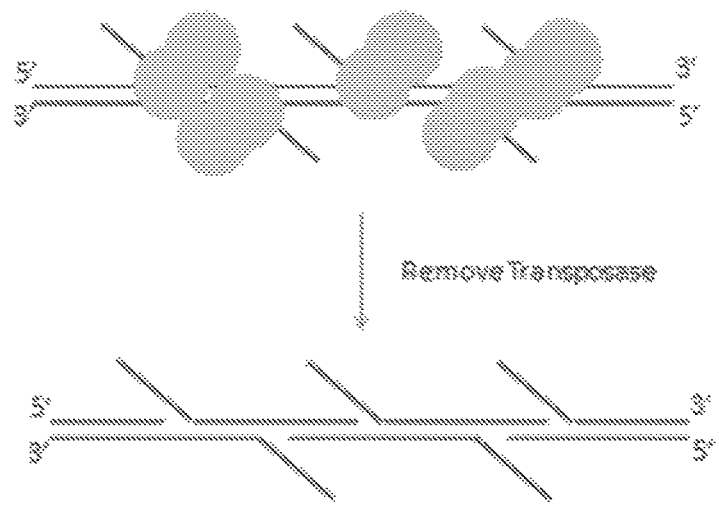
FIG. 8 shows one-ended transposition to create a modified nucleic acid having several inserts.

A further method for adding inserts to a target nucleic acid without necessarily fragmenting the target nucleic acid is one-ended transposition. One-ended transposition can be used to nick and directly attach an insert to only one strand of the target DNA at the site of transposition. A diagrammatic example is shown in FIG. 8. Various enzymes, including transposases can be used for one-ended transposition. For example, Mu, Tn5, and Rag-like transposase have been shown to display one-ended transposition. Certain mutants of Mu (e.g. Mu E392Q) show a preference for one-ended transposition over two-ended transposition (See Haapa et al. Nucl. Acids Res. 27:2777 (1999), which is incorporated herein by reference).

An exemplary method for achieving one-ended transposition is to use transposase dimers that are the product of mixing active and inactive transposase monomers. Inactive monomers can be created by mutagenesis, chemical modification or both. An appropriate ratio of active and inactive monomers for achieving an appropriate level of one-ended transposition can be determined based on statistical estimation (e.g. Poisson distribution) and/or titration assays. In particular embodiments, a transposase dimer can be formed from a mixture of active and inactive monomers that contains at most 50%, 25%, 10%, 5%, 1%, 0.1% or 0.01% active monomer.

Another method for achieving one-ended transposition is to use a mixture of reactive and non-reactive transposon elements along with an active transposase dimer. Exemplary non-reactive transposon elements include those that are blocked at the 3' end (e.g. via a dideoxy nucleotide at the 3' end or an extension blocking moiety at the 3' end). In particular embodiments, a transposon dimer can be formed from a mixture of reactive and non-reactive transposon elements that contains at most 50%, 25%, 10%, 5%, 1%, 0.1% or 0.01% reactive elements.

A further method that is contemplated for achieving one-ended transposition is to use a monomeric transposome. Monomeric transposomes are contemplated to result from modification or removal of dimerization contacts on a transposase protein. Removal can be achieved by mutagenesis of the monomer to delete a portion of the protein structure that forms the dimer contact and/or by point mutation to modify amino acids that participate in dimerization. Alternatively or additionally, the point of dimer contact can be modified by chemical modification (e.g. at a native amino acid that is present in the dimer contact region or at a mutated amino acid, such as reactive cysteine or lysine, that is introduced in the dimer contact region).

An insert used in a method or composition herein can include one or more priming site. In some embodiments, an insert contains a single type of priming site. Alternatively, an insert can include at least one, two or more priming sites. The orientation of the priming sites in such embodiments can be such that a primer hybridizing to the first priming site and a primer hybridizing to the second priming site are in the same orientation, or in different orientations. In one embodiment, the priming site sequence in the insert can be complementary to a primer used for amplification. Alternatively or additionally, the priming site sequence is complementary to a primer used for sequencing or other primer extension-based detection technique. In other embodiments two priming sites can be present in the insert, a first priming site that is complementary to an amplification primer and a second priming site that is complementary to a primer used for sequencing or other primer extension-based detection technique.

In some embodiments an insert includes a first priming site and a second priming site wherein one or more other moieties are disposed between the priming sites such as a cleavage site, binding moiety, linker or other moiety set forth below or elsewhere herein. Such embodiments can use a forked or Y-shaped adapter design useful for directional sequencing, as described in U.S. Pat. No. 7,741,463. An example is shown in FIG. 1.

In some embodiments, it can be advantageous to use inserts that have universal priming sites. For example, a target nucleic acid can be modified to include inserts that include pairs of universal priming sites, one on each strand. Universal priming sites can have various applications, such as serving as hybridization spots for primers used in amplifying, sequencing, and/or identifying target nucleic acids. When two priming sites are used, the first and second universal priming sites can be the same, substantially similar, similar, or different. In some embodiments, in order to prepare a target nucleic acid to include a first universal priming site (complementary to a first primer) and a second universal priming site (complementary to a second primer), a transposon element of an insert will include a first transposase recognition site and a second transposase recognition site, separated by a linker. The first priming site can include sequences that are the reverse complement of sequences within the second primer. In some embodiments, the first primer site comprises sequences having dyad symmetry to sequences within the second primer. In some embodiments, the first primer site comprises sequences having C2 symmetry to sequences within the second primer. A plurality of inserts may be inserted into a target nucleic acid by transposition in the presence of a transposase. The incorporated sequences may be cleaved to yield a plurality of target nucleic acid fragments, each comprising the first priming site and second priming site.

A first universal priming site and a second universal priming site can be incorporated into each target nucleic acid by a variety of methods. For example, target nucleic acids can be amplified using a first priming site and second priming site using tailed-oligonucleotides. As is understood in the art, a tailed-oligonucleotide can include sequences complementary to a primer site and additional sequences. In an example embodiment, a first tailed-oligonucleotide comprises sequences complementary to a first priming site and sequences for a first universal priming site, and a second tailed-oligonucleotide comprises sequences complementary to a second priming site and sequences for a second universal priming site. Further examples are set forth in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference. As will be understood, nucleic acid sequences comprising a first universal primer site and second universal primer site may be used in further sequencing methods.

An insert used in a method or composition of the present disclosure can include one or more cleavage sites. A modified nucleic acid polymer that includes an insert can then be cleaved at the cleavage site to produce fragments of the modified nucleic acid polymer. Cleavage sites that are susceptible to biochemical, chemical, physical or other cleavage mechanisms can be used. In some embodiments, a fragmentation site can include a nucleotide or nucleotide sequence that may be fragmented by various means. For example, a fragmentation site may be a substrate for an enzyme, such as a nuclease. Restriction endonuclease sites having nucleotide sequences that are specifically susceptible to cleavage with a respective restriction endonuclease can be particularly useful.

In another example, a fragmentation site can contain at least one ribonucleotide in a nucleic acid that may otherwise comprise deoxyribonucleotides and may be cleaved with an RNAse. Chemical cleavage agents capable of selectively cleaving the phosphodiester bond between a deoxyribonucleotide and a ribonucleotide can be used including, for example, metal ions such as rare-earth metal ions (e.g., $La^{3+}$, particularly $Tm^{3+}$, $Yb^{3+}$ or $Lu^{3+}$, Fe(3) or Cu(3)), or exposure to elevated pH.

In another example, a cleavage site can include one or more recognition sequences for a nickase, that is, a nicking endonuclease that breaks one strand of a double-stranded nucleic acid. Thus, the fragmentation site can include a first nickase recognition sequence, and optionally a second nickase recognition sequence. The first and second nickase recognition sequences can be the same as each other or different from each other.

In another example, a cleavage site can include one or more nucleotide analogues that comprise an abasic site and permits cleavage at the fragmentation site in the presence of certain chemical agents, such as polyamine, N,N'-dimethylethylenediamine (DMED) (see, for example, U.S. Pat. App. Pub. No. 2010/0022403, which is incorporated herein by reference). In some embodiments, an abasic site may be created by modification of a uracil nucleotide within the cleavage site, for example, using a uracil DNA glycosylase (UDG) enzyme. The polynucleotide strand including the abasic site may then be cleaved at the abasic site by treatment with endonuclease (e.g. Endo IV endonuclease, AP lyase, FPG glycosylase/AP lyase, Endo VIII glycosylase/AP lyase), heat or alkali. Abasic sites may also be generated at nucleotide analogues other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease such as Endo IV or AP lyase (see, for example, U.S. Patent Publication No. 2011/0014657, which is incorporated herein by reference).

In another example, a fragmentation site may include a diol linkage which permits cleavage by treatment with periodate (e.g., sodium periodate). In another example, a fragmentation site may include a disulfide group which permits cleavage with a chemical reducing agent, e.g. Tris (2-carboxyethyl)-phosphate hydrochloride (TCEP).

In some embodiments, a fragmentation site may include a photocleavable moiety. Photochemical cleavage can be carried out by any of a variety of methods that utilize light energy to break covalent bonds. A site for photochemical cleavage can be provided by a non-nucleotide chemical moiety in a nucleic acid, such as phosphoramidite [4-(4,4'-dimethoxytrityloxy)butyramidomethyl)-1-(2-nitrophenyl)-ethyl]-2-cyanoethyl-(N,N-diisopropyl)-phosphoramidite) (Glen Research, Sterling, Va., USA, Cat No. 10-4913-XX).

In some embodiments, a fragmentation site can include a peptide, for example, conjugate structure in which a peptide molecule is linked to a nucleic acid. The peptide molecule can subsequently be cleaved by a peptidase enzyme of the appropriate specificity, or by a suitable means of non-enzymatic chemical or photochemical cleavage. In some embodiments, a conjugate between peptide and nucleic acid will be formed by covalently linking a peptide to a nucleic acid, e.g., a strand of a double-stranded nucleic acid. Conjugates between a peptide and nucleic acid can be prepared using techniques generally known in the art. In one such technique the peptide and nucleic acid components of the desired amino acid and nucleotide sequence can be synthesized separately, e.g. by standard automated chemical synthesis techniques, and then conjugated in aqueous/organic solution. By way of example, the OPeC™ system commercially available from Glen Research is based on the native ligation of an N-terminal thioester-functionalized peptide to a 5'-cysteinyl oligonucleotide.

In particular embodiments, fragments of a modified nucleic acid polymer are produced by amplification of discrete portions of the polymer. For example, in some embodiments priming sites are inserted into the modified nucleic acid polymer and regions that are flanked by the priming sites can be amplified using primers that hybridize to the priming sites, for example, in a PCR amplification protocol or similar amplification method. It will be understood that in some embodiments, such as those that produce fragments by an amplification technique, a modified nucleic acid polymer need not include a cleavage site.

In cases where a modified nucleic acid is attached to a bead or other solid-phase carrier, fragments can be produced by destruction of the bead. For example, a hydrogel bead can be melted or dissolved to release fragments that were attached to the bead.

An insert can include one or more ligands. A ligand that is present in an insert can be a binding partner that is specific for a particular receptor. For example, the ligand can be specific for a receptor that is present on the surface of a solid support. As such, the receptor-ligand binding can facilitate surface capture of a modified nucleic acid or nucleic acid fragment that contains a portion of the insert having the ligand. Examples of ligands and receptors include biotin or polyHis that can bind streptavidin or nickel, respectively. Other examples include, pairs of ligands and their receptors known in the art, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC, HA, VSV-G, HSV, V5, and FLAG Tag™, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; nucleic acid strands and their complementary strands; and the like.

In some embodiments, an insert can include a reporter moiety. Useful reporter moieties include any of a variety of identifiable tags, labels, or groups known in the art. In certain embodiments, a reporter moiety can emit a signal. Examples of signals include those that are fluorescent, chemiluminescent, bioluminescent, phosphorescent, radioactive, calorimetric, or electrochemiluminescent. Exemplary reporter moieties include fluorophores, radioisotopes, chromogens, enzymes, antigens including epitope tags, semiconductor nanocrystals such as quantum dots, heavy metals, dyes, phosphorescent groups, chemiluminescent groups, electrochemical detection moieties, binding proteins, phosphors, rare earth chelates, transition metal chelates, near-infrared dyes, electrochemiluminescence labels, and mass spectrometer compatible reporter moieties, such as mass tags, charge tags, and isotopes. More reporter moieties that may be used with the methods and compositions described herein include spectral labels such as fluorescent dyes (e.g., fluorescein isothiocyanate, Texas red, rhodamine, and the like); radiolabels (e.g., $^3$H, $^{125}$I, $^{35}$S, $^{14}$C, $^{32}$P, $^{33}$P, etc.); enzymes (e.g., horseradish peroxidase, alkaline phosphatase etc.); spectral colorimetric labels such as colloidal gold or colored glass or plastic (e.g. polystyrene, polypropylene, latex, etc.); beads; magnetic labels; electrical labels; thermal labels; and mass tags.

In some embodiments, a plurality of different inserts can be used, wherein individual inserts can be distinguished by the presence of a unique barcode sequence. Thus a plurality of barcode-containing inserts can be added to a target nucleic acid to produce a modified nucleic acid polymer having a plurality of unique barcodes throughout. Exemplary barcodes, and methods for their preparation and use are set forth in PCT Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference. In alternative embodiments, it will be understood that such barcodes need not be used. This is possible, for example, when the connectivity or proximity information that is preserved by the methods set forth herein is sufficient to obtain an accurate representation of a nucleotide sequence for a target nucleic acid polymer without the need for the barcoding methods set forth in the above references. Thus, in particular embodiments, a plurality of inserts used in a method set forth herein will not include unique sequences (e.g. barcodes) compared to each other. Instead all of the inserts that are used in a method set forth herein, present in a modified nucleic acid polymer of the present disclosure, or present in a plurality of nucleic acid fragments of the present disclosure can have the same sequence (i.e. a universal sequence). Accordingly, some embodiments of the methods set forth herein will be carried out without distinguishing sequences of individual inserts (i.e. one insert from another) that may or may not be present in a modified nucleic acid polymer or fragment thereof A method of the present disclosure can include a step of releasing fragments of a modified nucleic acid polymer into a fluid. In some embodiments, each of the fragments will include at least a portion of the inserts that were previously added to the nucleic acid polymer. In particular embodiments the step can include (i) contacting the modified nucleic acid polymer with a solid support surface, and (ii) releasing the fragments of the modified nucleic acid polymer into the fluid. When a plurality of different modified nucleic acid polymers are contacted with the solid support surface it is generally beneficial to do so under conditions wherein individual modified nucleic acid polymers are spatially separated from each other. For example, the polymers can be delivered to vessel having a surface (e.g. the vessel can be a flow cell having a detection surface) at a relatively dilute concentration such that the average distance between nearest neighbor polymers in the vessel or on the surface is in the same relative range as the average distance that is desired for nearest neighbor fragments when captured on the surface. Similar spatial separation can be achieved by delivering modified nucleic acid polymers that are attached to beads. In the case where released fragments serve as templates for amplification to form clusters (or colonies) on the surface, the distance between nearest neighbor polymers can be in the range of the desired average pitch for clusters once they have been amplified on the surface.

Figure 2:
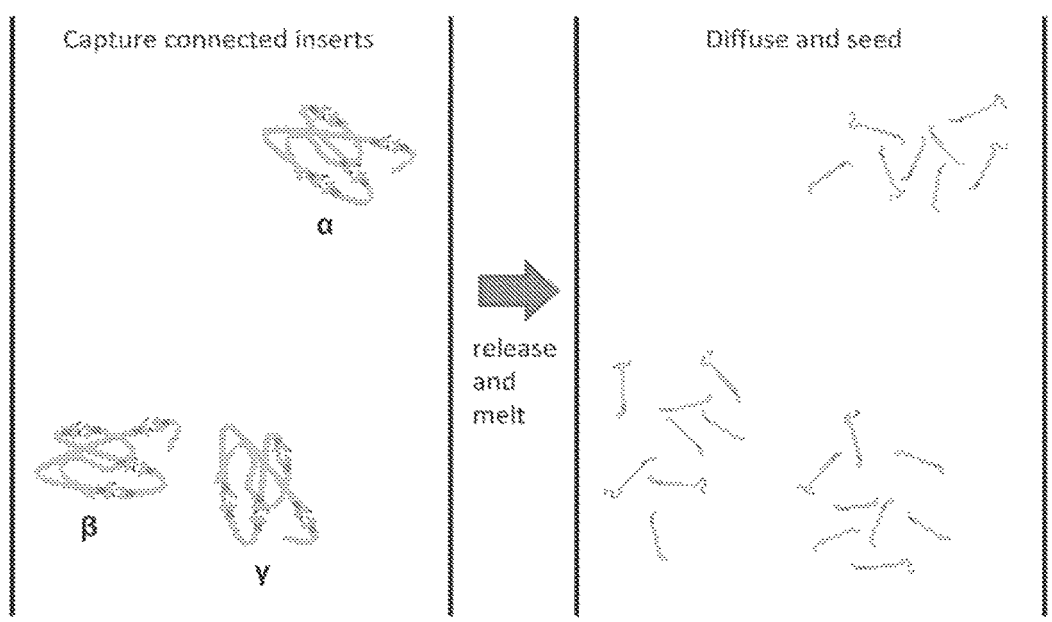
FIG. 2 shows a diagram of a flow cell that has captured insert-modified nucleic acid polymers at three separate regions (left panel) and the flow cell following cleavage and denaturation of the insert-modified nucleic acid polymers (right panel).

In particular embodiments a plurality of different modified nucleic acid polymers can be delivered to a flow cell (or other vessel) and allowed to diffuse (actively or passively) through a fluid that is in contact with a surface to which fragments will subsequently be attached. Thus, the polymers may be delivered in a stopped flow condition wherein a solution that carries the polymers is initially flowed into the flow cell and then the flow is stopped to allow diffusion. A diagrammatic example of an embodiment where three different modified nucleic acid polymers are allowed to diffuse to locations along the surface of a flow cell is shown in FIG. 2. As exemplified by the figure, the solid support surface can optionally include a capture moiety that will bind to a binding partner present on the polymers. Any of a variety of receptors and ligands set forth herein or otherwise known in the art can be used for this purpose. Thus, the inserts can include ligands and the solid support surface can include receptors for the ligands, such that contacting of the modified nucleic acid polymers with the solid support surface attaches the modified nucleic acid polymers to the surface.

A modified nucleic acid can be attached to a solid-phase carrier such as a bead and the bead can be delivered to a vessel having a solid phase surface. FIG. 5 shows an exemplary modified target nucleic acid on a bead. FIG. 6 shows another example of a modified target nucleic acid on a bead. A solid-phase carrier having a target nucleic acid, modified nucleic acid or fragments thereof can be allowed to contact a solid support surface (e.g. via gravity settling) and in some cases can be attached to the surface using receptors and ligands or other means set forth herein.

Once one or more different modified nucleic acids are present at or near respective regions of solid support surface, fragments of the modified nucleic acids can be produced. In some embodiments, the different modified nucleic acid polymers can be cleaved such that fragments of the polymers are produced. Cleavage can occur at cleavage sites that are present in the inserts that have been integrated into the modified nucleic acid polymers. Alternatively or additionally, fragments can be produced by amplifying sequence regions of the modified nucleic acids. For example, amplification can be carried out using primers that anneal to priming sites on inserts that have been added to the modified nucleic acids. Denaturation can optionally be carried out to create single stranded versions of the fragments. The fragments that are produced from one or more modified nucleic acid polymers can be captured randomly at locations on a solid support surface, as set forth in further detail below.

As an alternative to passive diffusion of modified nucleic acid polymers, or fragments thereof, active transport techniques can be used to move the molecules to a desired location or to influence the spatial configuration of the molecules. A particularly useful active transport techniques is electric field assisted (e-field assist) transport. For example, one or more regions of an array can be electrically coupled to a power source to produce an electric charge that attracts target nucleic acid polymers or fragments thereof. In one configuration, a positive charge can attract nucleic acids via the negatively charged sugar-phosphate backbone. Exemplary methods and apparatus for using e-field assist to attract nucleic acids to surfaces are described in US Pat. App. Pub. No. 2009/0032401 A1 or U.S. patent application Ser. No. 13/783,043, each of which is incorporated herein by reference. Other useful techniques for actively transporting nucleic acids include, but are not limited to, fluid flow under positive or negative pressure, gravitational force induced by centrifugation, movement along chemical or temperature gradients, and the like.

The spatial configuration of modified nucleic acid polymers can be manipulated in a method set forth herein. In particular embodiments, the polymers can be induced to fold into relatively compact configurations, for example, using chemical, temperature or electrical conditions. Exemplary conditions for creating compact formations include those used to create DNA nanoballs as set forth in US Pat. App. Pub. No. 2008/0242560 A1 or US Pat. App. Pub. No. 2008/0234136 A1, each of which is incorporated herein by reference. Alternatively, one or more of the modified nucleic acid polymers can be stretched or otherwise configured in an elongated configuration. For example, the polymers can be attached on the surface (e.g. at or near an end of the polymer) and elongated along a region of the surface. The fragments derived from the polymers can eventually be attached to the regions of the surface according to a method set forth herein. Exemplary techniques for elongating nucleic acid polymers include, but are not limited to, fluid flow stretching, weak force stretching, e-field assisted stretching or other methods known in the art such as those described in US Pat. App. Pub. No. 2012/0129704 A1, which is incorporated herein by reference. Accordingly, a method of the invention can include a step of (i) stretching a modified nucleic acid polymer along a solid support surface, and (ii) releasing fragments of the modified nucleic acid polymer into a fluid.

Conditions can be selected in a method of the present disclosure to obtain fragments of a desired length. For example, the length can be influenced by conditions used for attaching inserts to a target nucleic acid polymer. In cases where the inserts contain cleavage sites, the length of fragments resulting from cleavage will be related to the average distance between inserts in the polymers. The average size of the fragments can also be influenced by the degree of completion to which a cleavage reaction is allowed to proceed. A cleavage reaction that goes to substantial completion will produce fragments that are correlated with the average distance between cleavage sites in the modified nucleic acid polymer, whereas cleavage reaction that go to partial completion will produce fragments of a larger average length than the average distance between cleavage sites.

In some embodiments, the absolute or average fragment length can be at least about 5, 10, 20, 30, 40, 50, 60, 70, 80, 90, 100, or more nucleotides. In some embodiments, the absolute or average fragment length can be at least about 100, 200, 300, 400, 500, 600, 700, 800, 900, 1000, or more nucleotides. In some embodiments, the absolute or average fragment length can be at least about 1 kb, 2 kb, 3 kb, 4 kb, 5 kb, 6 kb, 7 kb, 8 kb, 90 kb, 100 kb, or more nucleotides. In some embodiments, the absolute or average fragment length can be at least about 100 kb, 200 kb, 300 kb, 400 kb, 500 kb, 600 kb, 700 kb, 800 kb, 900 kb, 1000 kb, or more nucleotides. Alternatively or additionally to the threshold values set forth above, the absolute or average fragment length can be at most about 1000 kb, 500 kb, 100 kb, 10 kb, 5 kb, 1 kb, 500 bases, 100 bases, 50 bases or 10 bases or less.

In some embodiments, a target nucleic acid, modified nucleic acid or nucleic acid fragment can be attached to the surface of a solid support. Solid supports can be two- or three-dimensional and can be a planar surface (e.g., a glass slide) or can be shaped. Useful materials include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. Suitable three-dimensional solid supports include, for example, spheres, microparticles, beads, membranes, slides, plates, micromachined chips, tubes (e.g., capillary tubes), microwells, microfluidic devices, channels, filters, or any other structure suitable for anchoring a nucleic acid. Solid supports can include planar microarrays or matrices capable of having regions that include populations of nucleic acids or primers. Examples include nucleoside-derivatized CPG and polystyrene slides; derivatized magnetic slides; polystyrene grafted with polyethylene glycol, and the like.

Various methods can be used to attach, anchor or immobilize nucleic acids to the surface of a solid support. The attachment can be achieved through direct or indirect bonding to the surface. The bonding can be by covalent linkage. See Joos et al. (1997) *Analytical Biochemistry*, 247:96-101; Oroskar et al. (1996) *Clin. Chem.*, 42:1547-1555; and Khandjian (1986) *Mol. Bio. Rep.*, 11:107-11, each of which is incorporated herein by reference. A preferred attachment is direct amine bonding of a terminal nucleotide of a nucleic acid to an epoxide integrated on the surface. The bonding also can be through non-covalent linkage. For example, biotin-streptavidin (Taylor et al. (1991) *J. Phys. D: Appl. Phys.*, 24:1443, which is incorporated herein by reference) and digoxigenin with anti-digoxigenin (Smith et al., *Science*, 253:1122 (1992), which is incorporated herein by reference) are common tools for anchoring nucleic acids to surfaces.

Attachment of a nucleic acid to a surface can be via an intermediate structure such as a bead, particle or gel. Attachment of nucleic acids to an array via a gel is exemplified by flow cells available commercially from Illumina Inc. (San Diego, Calif.) or described in US Pat. App. Publ. Nos. 2010/0111768 A1 or 2012-0270305 A1; or WO 05/065814, each of which is incorporated herein by reference. Exemplary gels that can be used in the methods and apparatus set forth herein include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. Prov. Pat. App. Ser. No. 61/753,833 and WIPO App. Ser. No. PCT/US2013/044305, each of which is incorporated herein by reference).

Although the present disclosure sets forth several embodiments in which a target nucleic acid is modified prior to being attached to a solid support surface, it will be understood that a target nucleic acid need not be modified prior to attachment. For example, a target nucleic acid can be attached to a solid support prior to being modified by the methods set forth herein. Transposase treatment can occur after a target nucleic acid has been attached to a solid support surface. An exemplary embodiment is diagrammed in FIG. 7, where a target nucleic acid is attached to a surface (Panel A), treated with transposases to produce a plurality of fragment via tagmentation (Panel B), resulting in release into solution of several fragments that contain inserts (Panel C). The fragments can be captured randomly at sites in a region of the solid support surface. In embodiments where a plurality of different target nucleic acids are attached to different regions of the surface, fragments can be released and captured under conditions where the fragments from each target nucleic acid randomly end up at different locations within the respective regions. The captured fragments can be optionally amplified and/or detected as set forth in further detail herein.

For embodiments that utilize transposases to attach inserts to a target nucleic acid polymer, the transposases may either be present at the time that the insert-modified nucleic acid polymer is contacted with the surface of a substrate or the transposases can be removed from the insert-modified nucleic acid polymer prior to making the contact. In particular embodiments the transposase can include a receptor or ligand that binds to a respective ligand or receptor on the surface of the solid support. Alternatively or additionally, the ligand or receptor that mediates binding to a solid support can be present in the insert of the modified nucleic acid polymer. Thus, the insert can mediate binding to the surface whether or not transposases are attached to the modified nucleic acid polymer. Transposases can be removed from nucleic acids using methods known in the art such as thermal denaturation, chemical denaturation (e.g. surfactant treatment), or treatment with one or more proteases.

In many embodiments, a solid support to which nucleic acids are attached in a method set forth herein will have a continuous or monolithic surface. Thus, fragments can attach at spatially random locations wherein the distance between nearest neighbor fragments (or nearest neighbor clusters derived from the fragments) will be variable. The resulting arrays will have a variable or random spatial pattern of features. Alternatively, a solid support used in a method set forth herein can include an array of features that are present in a repeating pattern. In such embodiments, the features provide the locations to which modified nucleic acid polymers, or fragments thereof, can attach. Particularly useful repeating patterns are hexagonal patterns, rectilinear patterns, grid patterns, patterns having reflective symmetry, patterns having rotational symmetry, or the like. The features to which a modified nucleic acid polymer, or fragment thereof, attach can each have an area that is smaller than about 1 mm$^2$, 500 μm$^2$, 100 μm$^2$, 25 μm$^2$, 10 μm$^2$, 5 μm$^2$, 1 μm$^2$, 500 nm$^2$, or 100 nm$^2$. Alternatively or additionally, each feature can have an area that is larger than about 100 nm$^2$, 250 nm$^2$, 500 nm$^2$, 1 μm$_2$, 2.5 μm$^2$, 5 μm$^2$, 10 μm$^2$, 100 μm$^2$, or 500 μm$^2$. A cluster or colony of nucleic acids that result from amplification of fragments on an array (whether patterned or spatially random) can similarly have an area that is in a range above or between an upper and lower limit selected from those exemplified above.

For embodiments that include an array of features on a surface, the features can be discrete, being separated by interstitial regions. Alternatively, some or all of the features on a surface can be abutting (i.e. not separated by interstitial regions). Whether the features are discrete or abutting, the average size of the features and/or average distance between the features can vary such that arrays can be high density, medium density or lower density. High density arrays are characterized as having features with average pitch of less than about 15 μm. Medium density arrays have average feature pitch of about 15 to 30 μm, while low density arrays have average feature pitch of greater than 30 μm. An array useful in the invention can have feature pitch of, for example, less than 100 μm, 50 μm, 10 μm, 5 μm, 1 μm or 0.5 μm. Alternatively or additionally, the feature pitch can be, for example, greater than 0.1 μm, 0.5 μm, 1 μm, 5 μm, 10 μm, 50 μm, or 100 μm.

Several commercially available sequencing platforms rely on substrates having wells that provide a barrier to the diffusion of detection reagents (e.g. pyrophosphate in platforms available from 454 LifeSciences (a subsidiary of Roche, Basel Switzerland) or protons in platforms available from Ion Torrent (a subsidiary of Life Technologies, Carlsbad Calif.)) during sequence detection steps. The methods set forth herein can be advantageous for delivering fragments of a modified nucleic acid to the wells in a way that phasing or proximity information is preserved.

A method of the present disclosure can include a step of capturing fragments from a modified nucleic acid polymer on a solid support surface. Generally, the fragments have previously been released from the polymer into a fluid and are then captured from the fluid such that the fragments randomly end up at particular locations on the surface. The locations can be on a monolithic or continuous surface or alternatively the locations can be prefabricated features on a patterned array. As such, the locations to which the fragments attach can be random with regard to predictability or knowledge of where any specific fragment will attach (i.e. what nucleic acid sequence will be present at a particular location), whether or not the spatial pattern of the features is random.

Fragments that are in a fluid can be transported randomly to locations on a surface via passive diffusion or active transport. Exemplary conditions and techniques that can be used for such transport are known in the art or exemplified herein in the context of transporting modified nucleic acids to a surface.

A method of the present disclosure can further include a step of amplifying fragments at locations on a surface to produce amplified fragments. The amplified fragments can be detected, for example, via a nucleic acid sequencing technique as set forth below. In particular embodiments, the fragments can be amplified using at least one primer that is attached to the surface. A primer that is used for amplification can, at least in some configurations, hybridize to a priming site on an insert. The primer can be extended to produce the amplified fragments that are attached to the surface, for example at particular locations. Solid-phase extension methods can be used as set forth in further detail below.

A method of the present disclosure can include a step of amplifying portions of a target nucleic acid, modified nucleic acid, or fragments thereof. Any suitable amplification methodology known in the art can be used. In some embodiments, nucleic acid fragments are amplified on a solid support. For example, in some embodiments, the nucleic acid fragments are amplified using bridge amplification methodologies as exemplified by the disclosures of U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. Bridge amplification methods allow amplification products to be immobilized on a solid support in order to form arrays comprised of clusters (or "colonies") of immobilized nucleic acid molecules. Each cluster or colony on such an array is formed from a plurality of identical immobilized polynucleotide strands and a plurality of identical immobilized complementary polynucleotide strands. The arrays so-formed can be referred to herein as "clustered arrays". The products of solid-phase amplification reactions are so-called "bridged" structures when formed by annealed pairs of immobilized polynucleotide strands and immobilized complementary strands, both strands being immobilized on the solid support at the 5' end, preferably via a covalent attachment. Bridge amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR, solid-phase MDA, solid-phase RCA etc. whether one or both primers of each pair of amplification primers are immobilized.

In other embodiments, target nucleic acids, modified nucleic acids, or fragments thereof are amplified in solution. For example, in some embodiments, amplification primers are hybridized to priming sites of inserts in solution. In other embodiments, amplification primers are hybridized to the inserts when modified nucleic acids or fragments thereof are attached to a solid support.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference. The above amplification methods can be employed to amplify one or more nucleic acids of interest. For example, PCR, multiplex PCR, SDA, TMA, NASBA and the like can be utilized to amplify immobilized nucleic acid fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., *Nat. Genet.* 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, each of which is incorporated herein by reference). It will be appreciated that these amplification methodologies can be designed to amplify immobilized nucleic acid fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate® assay (Illumina, Inc., San Diego, Calif.) as exemplified by U.S. Pat. Nos. 7,582,420 and 7,611,869, each of which is incorporated herein by reference in its entirety.

An isothermal amplification technique can be used in a method of the present disclosure. Exemplary isothermal amplification methods include, but are not limited to, Multiple Displacement Amplification (MDA) as exemplified by, for example, Dean et al., *Proc. Natl. Acad. Sci. USA* 99:5261-66 (2002) or isothermal strand displacement nucleic acid amplification as exemplified by, for example U.S. Pat. No. 6,214,587, each of which is incorporated herein by reference. Other non-PCR-based methods that can be used in the present disclosure include, for example, strand displacement amplification (SDA) which is described in, for example Walker et al., *Molecular Methods for Virus Detection*, Academic Press, Inc., 1995; U.S. Pat. Nos. 5,455,166, and 5,130,238, and Walker et al., *Nucl. Acids Res.* 20:1691-96 (1992) or hyperbranched strand displacement amplification which is described in, for example Lage et al., *Genome Research* 13:294-307 (2003), each of which is incorporated herein by reference. Additional description of amplification reactions, conditions and components are set forth in U.S. Pat. No. 7,670,810, which is incorporated herein by reference. Other useful isothermal amplification techniques include recombinase-facilitated amplification techniques such as those sold commercially as TwistAmp™ kits by TwistDx (Cambridge, UK). Useful components of recombinase-facilitated amplification reagent and reaction conditions are set forth in U.S. Pat. No. 5,223,414 and U.S. Pat. No. 7,399,590, each of which is incorporated herein by reference. Helicase dependent amplification can also be used, for example, as described in Xu et al. *EMBO Rep* 5:795-800 (2004), which is incorporated herein by reference.

In some embodiments, it may be desirable to perform a re-seeding step. For example, nucleic acid fragments can be captured at locations within a region of a surface, replicated on one or more cycles of an amplification process, the original fragments and/or amplicons thereof can be released from the locations, the released nucleic acids can be captured at other locations in the same region, and the newly captured nucleic acids can be amplified. In a specific example, a single cycle of bridge amplification can be carried out for a fragment that was seeded on a surface and instead of washing away the original template fragment upon release from the surface, the template fragment can re-seed the surface at a new location that is proximal to the location where it had originally seeded. Subsequent rounds of bridge amplification will allow cluster growth at both the original seed location and at the re-seed location. Using such methods replicate colonies can be created at a region of a surface to provide technical replicates. Analysis of the sequences for the technical replicates can provide the benefit of error checking. For example, observed sequence variants that occur in only a subset of proximal clusters (that are identified as technical replicates) can be identified as amplification errors, whereas sequence variants that occur in all clusters that are identified as technical replicates for a particular fragment are more likely to be true variants.

The methods described herein can include a step of sequencing fragments derived from a target nucleic acid. One example is sequencing-by-synthesis (SBS). In SBS, extension of a nucleic acid primer along a nucleic acid template (e.g. a fragment of a target nucleic acid or amplicon thereof) is monitored to determine the sequence of nucleotides in the template. The primer can hybridize to a priming site that is present in an insert as set forth above. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array using steps set forth herein can be subjected to an SBS technique under conditions where events occurring for different templates can be distinguished due to their location in the array.

Flow cells provide a convenient format for housing an array of nucleic acid fragments that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid fragments. Those sites of an array where primer extension (e.g. via hybridization of the primer to a priming site located on an insert attached to a nucleic acid fragment) causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. No. 6,210,891; U.S. Pat. No. 6,258,568 and U.S. Pat. No. 6,274,320, each of which is incorporated herein by reference). In pyrosequencing, released PPi can be detected by being converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to methods of the present disclosure are described, for example, in WIPO Pat. App. Ser. No. PCT/US11/57111, US 2005/0191698 A1, U.S. Pat. No. 7,595,883, and U.S. Pat. No. 7,244,559, each of which is incorporated herein by reference.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both Sequencing-by-ligation and sequencing-by-hybridization procedures, target nucleic acid fragments (or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); and Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference.

A sequencing step of the present methods can include a nanopore sequencing technique such as those described in Deamer & Akeson *Trends Biotechnol.* 18, 147-151 (2000); Deamer & Branton, *Acc. Chem. Res.* 35:817-825 (2002); and Li et al., *Nat. Mater.* 2:611-615 (2003), each of which is incorporated herein by reference. In such embodiments, the target nucleic acid fragment passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni & Meller *Clin. Chem.* 53, 1996-2001 (2007); Healy, *Nanomed.* 2:459-481 (2007); and Cockroft et al., *J. Am. Chem. Soc.* 130:818-820 (2008), each of which is incorporated herein by reference). In some embodiments, the location of individual nanopores is akin to a site or feature on the arrays exemplified herein. The proximity of nanopores to each other can be correlated with the proximity of fragment sequences they read, for example, to facilitate assembly of those fragments into the larger sequence from which they were derived.

The sequencing steps described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, or fragments thereof, the target nucleic acids, or fragments, can be in an array format. In an array format, fragments of target nucleic acids can be typically coupled to a surface in a spatially distinguishable manner, for example, using attachment techniques set forth herein. The array can include a single copy of a target nucleic acid fragment at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, $10^7$ features/cm$^2$, $5 \times 10^7$ features/cm$^2$, $10^8$ features/cm$^2$, $5 \times 10^8$ features/cm$^2$, $10^9$ features/cm$^2$, $5 \times 10^9$ features/cm$^2$, or higher.

A method of the present disclosure can include a step of determining haplotype phase for polymorphisms occurring in the nucleotide sequences for different fragments released from a modified nucleic acid polymer. Accordingly, a representation of nucleotide sequence for a target nucleic acid polymer can include a representation of haplotype phase for alleles occurring in the nucleotide sequences for at least two different fragments released from the modified nucleic acid polymer.

A method of the present disclosure can include a step of comparing complementary sequences determined for proximal locations on the solid support surface to identify sequence errors.

In accordance with the methods set forth herein, the relative proximity of any two fragment species on a solid support can provide information useful for alignment of sequence information obtained from the two fragments. Specifically, the distance between clusters, derived from any two given fragments, on a solid support can be positively correlated with the probability that the two clusters are from the same target polynucleotide molecule, as described in greater detail in WO 2012/025250, which is incorporated herein by reference. Similarly, the distance between clusters, derived from any two given fragments, on a solid support can be positively correlated with the probability that the two clusters are from a common source (since all fragments of a particular target polynucleotide will have come from the source of that target polynucleotide).

As an example, in some embodiments, fragments derived from a long nucleic acid molecule captured at the surface of a flowcell occur in a line across the surface of the flowcell (e.g. if the nucleic acid was stretched out prior to fragmentation or amplification) or in a cloud on the surface (e.g. if the nucleic acid was clumped as shown in FIG. 2). Further, a physical map of the immobilized nucleic acid can then be generated. The physical map thus correlates the physical relationship of clusters after immobilized nucleic acid is amplified. Specifically, the physical map is used to calculate the probability that sequence data obtained from any two clusters are linked, as described in the incorporated materials of WO 2012/025250. Alternatively or additionally, the physical map can be indicative of the genome of a particular organism in a metagenomic sample. In this latter case the physical map can indicate the order of sequence fragments in the organism's genome; however, the order need not be specified and instead the mere presence of two or more fragments in a common organism (or other source or origin) can be sufficient basis for a physical map that characterizes a mixed sample and one or more organisms therein.

In some embodiments, the physical map is generated by imaging the solid support to establish the location of the immobilized nucleic acid molecules across the surface. In some embodiments, the immobilized nucleic acid is imaged by adding an imaging agent to the solid support and detecting a signal from the imaging agent. In some embodiments, the imaging agent is a detectable label. Suitable detectable labels, include, but are not limited to, protons, haptens, radionuclides, enzymes, fluorescent labels, chemiluminescent labels, and/or chromogenic agents. For example, in some embodiments, the imaging agent is an intercalating dye or non-intercalating DNA binding agent. Any suitable intercalating dye or non-intercalating DNA binding agent as are known in the art can be used, including, but not limited to those set forth in U.S. 2012/0282617, which is incorporated herein by reference.

In certain embodiments, a plurality of modified nucleic acid molecules is flowed onto a flowcell comprising a plurality of nano-channels. As used herein, the term nano-channel refers to a narrow channel into which a long linear nucleic acid molecule is stretched. In some embodiments, no more than 1, 2, 3, 4, 5, 6, 7, 8, 9, 10, 11, 12, 13, 14, 15, 16, 17, 18, 19, 20, 30, 40, 50, 60 70, 80, 90, 100, 200, 300, 400, 500, 600, 700, 800, 900 or no more than 1000 individual long strands of nucleic acid are stretched across each nano-channel. In some embodiments the individual nano-channels are separated by a physical barrier that prevents individual long strands of target nucleic acid from interacting with multiple nano-channels. In some embodiments, the solid support comprises at least 10, 50, 100, 200, 500, 1000, 3000, 5000, 10000, 30000, 50000, 80000 or at least 100000 nano-channels.

In some embodiments, the nucleic acids have been modified to include inserts having cleavage sites and the cleavage sites are cleaved once the nucleic acids have been stretched along the channel. The resulting fragments can be optionally amplified to form clusters along the surface of the channel. Contiguity mapping can then be performed, for example, by following the clusters down the length of one of these channels. As an example, a flowcell having 1000 or more nano-channels with mapped immobilized fragmentation products in the nano-channels can be used to sequence the genome of an organism with short 'positioned' reads. In some embodiments, mapped immobilized fragmentation products in the nano-channels can be used to resolve haplotypes. In some embodiments, mapped immobilized fragmentation products in the nano-channels can be used to resolve phasing issues.

Figure 11:
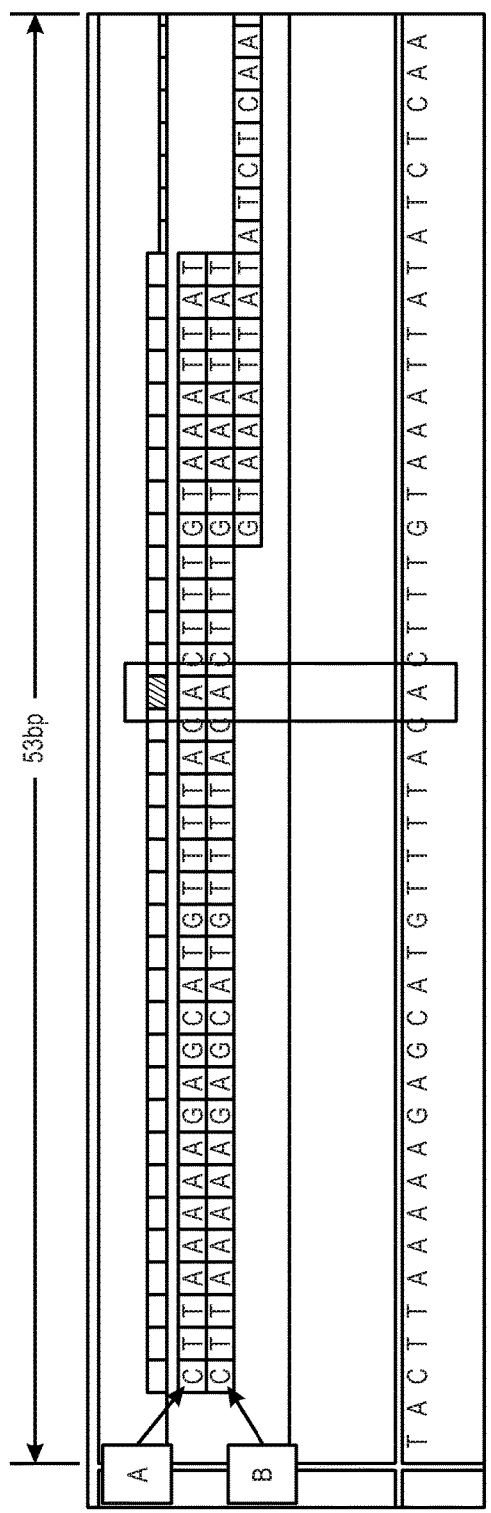
FIG. 11 shows an example of error correction from two sequencing reads A and B. Sequencing reads A and B differ from the reference genome at the same position (C for A substitution). The clusters which generated reads A and B are 350 µm distant from one another on the flow cell, which is well beyond what might be caused by an sequencing artifact, yet within the average radius for proximal groups (200-300 μm).

In some embodiments, the methods of the above aspects of the invention can be used for error correction of the sequencing reads. FIG. 11 shows an example of such error correction. Two sequencing reads A and B differ from the reference genome at the same position (C for A substitution). The clusters which generated reads A and B are 350 µm distant from one another on the flow cell. This distance is well beyond what might be caused by an sequencing artifact, yet within the average radius for proximal groups (200-300 µm). From this, coupled with the fact that the two reads have identical start-stop positions and their orientations reversed, it can be inferred that they started as complementary fragments and that the C mutation shown here is not an artifact of the sample preparation or sequencing.

In some embodiments, the methods of the above aspects of the invention can be used for gene expression analysis. In some embodiments, the target mRNA is from a single cell. In some embodiments, mRNA can be captured on beads comprising oligo d(T) probes.

Various combinations of the components set forth above in regard to exemplary reaction mixtures and reaction methods can be provided in a kit form. Such a kit can include individual components that are separated from each other, for example, being carried in separate vessels or packages. A kit can include one or more sub-combinations of the components set forth herein, the one or more sub-combinations being separated from other components of the kit. The sub-combinations can be combinable to create a reaction mixture set forth herein (or combined to perform a method set forth herein). In particular embodiments, a sub-combination of components that is present in an individual vessel or package is insufficient to perform all steps of a method set forth herein. However, the kit as a whole can include a collection of vessels or packages the contents of which can be combined to perform a method set forth herein.

A kit can include a suitable packaging material to house the contents of the kit. The packaging material can be constructed by well known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, cardboard, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for adding an insert to a nucleic acid polymer, cleaving a modified nucleic acid polymer to produce fragments or determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and from where they can be obtained.

The following examples are intended to illustrate but not limit the present invention.

Example I

Figure 1B:
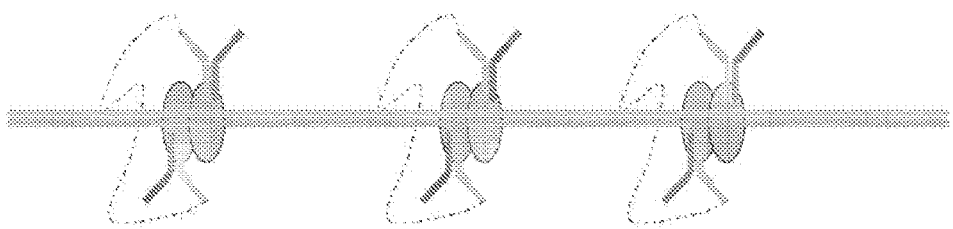
FIG. 1B shows a diagram of a formation of looped complexes between transposases and the linked transposon elements attached to a nucleic acid polymer.
Figure 1C:
FIG. 1C shows a diagram of a modified form of the nucleic acid polymer that includes inserts containing the linked transposon elements.

Preserving Connectivity Information in Cluster Arrays Using Linked Transposons to Integrate Inserts into Genomic DNA Two transposon elements are linked together as shown in FIG. 1A. Each transposon element forms a forked adapter construct, having two strands that from an annealed double stranded portion and a non-annealed portion. The annealed portion includes complementary portions of each strand that form a mosaic element (ME). The non-annealed portion includes a P5 priming site near the 5' end of one strand and a P7 priming site near the 3' end of the other strand. The two transposons are identical and linked together through the 5' ends of the non-annealed portions (i.e. the 5' ends of the strands containing the P5 priming sites). The linked transposon elements bind to respective transposase subunits to form a transposome complex that is in the form of a looped complex and several of the looped complexes bind to a target genomic DNA polymer (FIG. 1B). The linker keeps the target DNA from fragmenting at the time of transposition (i.e. "tagmentation" is inhibited despite insertion of the linked transposon elements as shown in FIG. 1C). As a result of the 5' to 5' linkage, the modified nucleic acid polymer will include sequence portions from alternate strands of the target nucleic acid polymer concatenated into a single polymer strand. The inserts include cleavage sites that are present in the linker, and optionally a binding moiety is also present in the linker.

The target nucleic acid polymers that have been modified to include the inserts are then loaded into a flow cell and captured on the surface of the flow cell by a receptor that is specific for the binding moiety. For example, in the case where the linker contains a specific nucleic acid sequence the flow cell can include capture probes with sequences that are complementary to the specific sequence or alternatively the linker can include a biotin analog that binds to streptavidin that is attached to the surface of the flow cell. The insert-modified genomic DNA is attached to the flow cell surface in double stranded form as shown in FIG. 2. Under non-flow conditions, individual insert-modified genomic DNA polymers will bind in a localized region of the surface. The linkers can then be cleaved and the strands denatured to allow individual fragments (for example in the range of 200 b to 100 kb) to diffuse away from each other and seed on the flow cell as shown on the right hand panel of FIG. 2. The diffusion conditions are selected to allow the fragments to seed locations that are proximal to the localized region where the insert-modified genomic DNA polymer is attached. The diffusion conditions are selected to allow this localization while preventing the fragments from being too closely spaced, instead seeding as templates that can form micron-sized monoclonal clusters in a subsequent bridge amplification step. Once the templates have been seeded and bridge-amplified as shown in FIG. 3, sequencing can proceed on a HiSeq or MiSeq platform (Illumina Inc., San Diego, Calif.) using standard protocols.

Figure 3:
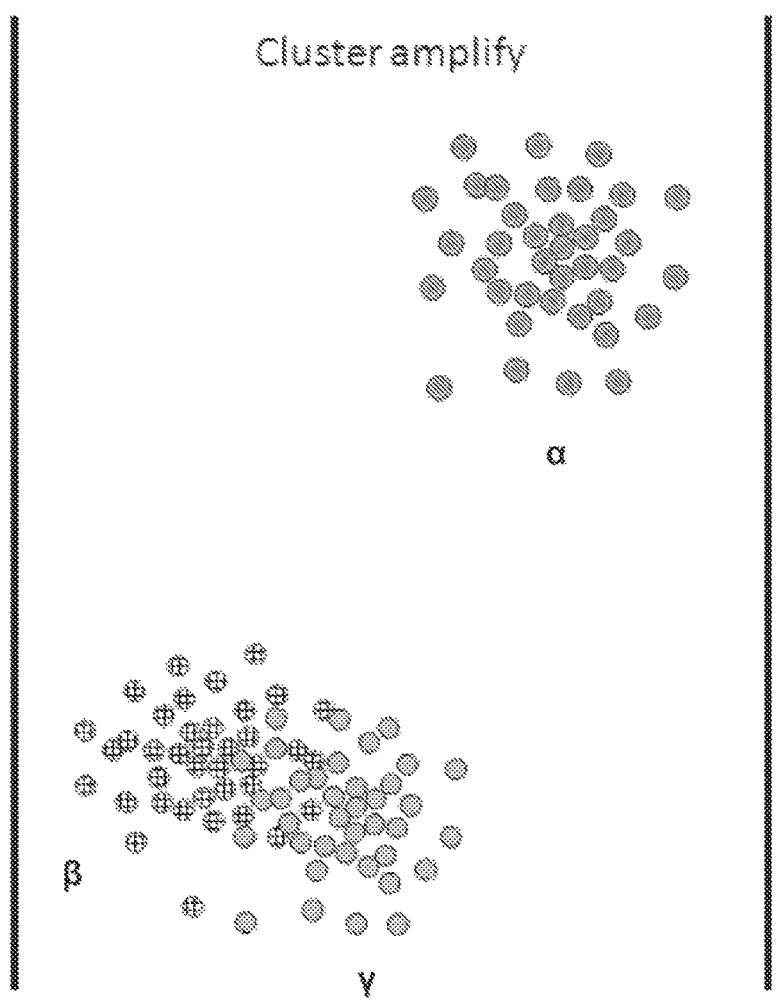
FIG. 3 shows a diagram of cluster clouds resulting from the nucleic acid fragments captured on the flow cell of FIG. 2 and subsequent bridge amplification of the captured fragments.

As exemplified by comparison of the locations of the three populations of clusters in FIG. 3 to the region where the three insert-modified genomic DNA polymers bound to the flow cell surface in FIG. 2, clusters which come from adjacent or overlapping genomic regions form cluster clouds. Some cluster clouds may be distinct from other cluster clouds as is exemplified for cloud α which is distinct from cloud β and from cloud γ. Cluster-clouds can intermingle without problem, as exemplified for cloud β and cloud γ. Thus, a flow cell can be clustered at relatively high densities.

Sequence analysis is then carried out. During assembly, adjacent reads are grouped based on a distance metric (e.g. normalized physical separation between clusters in a flow cell) to assess whether two reads should be assembled together, considered phased, or used to correct errors in each other. Nearby reads can be assembled and phased even across repetitive regions, and complementary reads which are in close proximity to each other can be compared against each other for robust error correction.

Figure 4A:
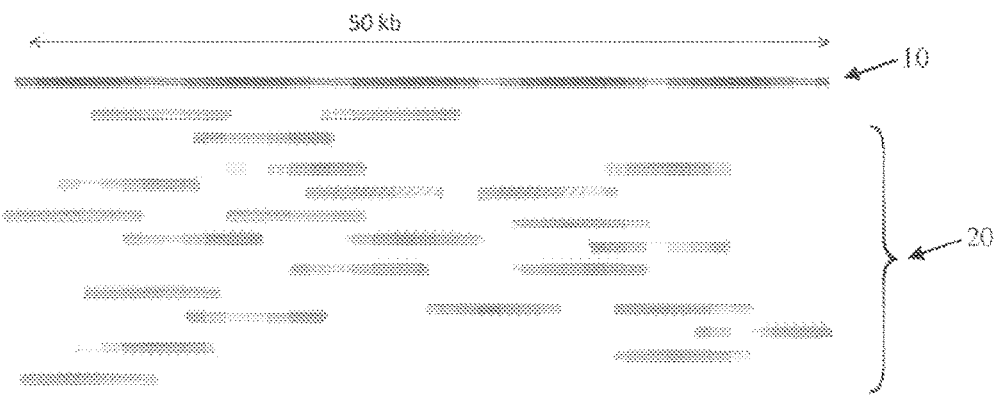
FIG. 4A shows diagram of sequence reads aligned with a 50 kb reference sequence absent knowledge of cluster proximity information.
Figure 4B:
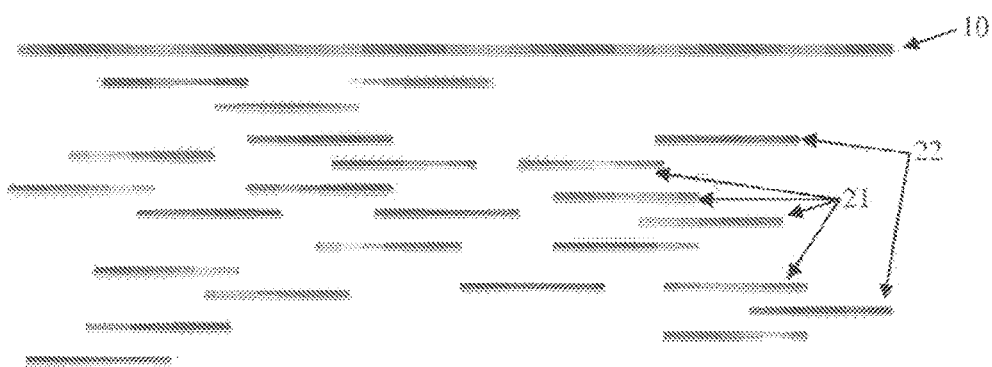
FIG. 4B shows a diagram of sequence reads aligned with the 50 kb reference genome sequence where reads from two different genomic DNA molecules.
Figure 4C:
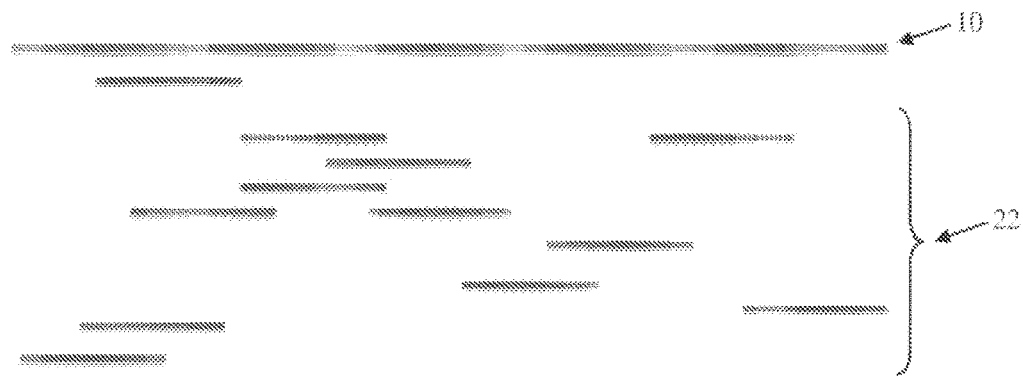
FIG. 4C shows a diagram of sequence reads for fragments from one of the genomic DNA molecules aligned with the 50 kb reference genome sequence.

Normally, it is unknown which sequence reads obtained for individual clusters on a flow cell came from a common original molecule. This is exemplified by the monochromatic collection of fragment reads 20 aligned against the 50 kb reference sequence 10 in FIG. 4A. However, using the distance information on the flow cell produced by the method above, reads are grouped into sets whose distances are consistent with having come from either a first genomic DNA molecule (light grey fragments 21 in FIG. 4B) or from a second genomic DNA molecule (dark grey fragments 22 in FIG. 4B). Accordingly, the set of fragments 22 from the second genomic DNA molecule can be assembled into a phased contig as shown in FIG. 4C.

Using the methods exemplified above, homogenous and heterogeneous loci among the sets can be used to assemble phased contigs; de novo assembly can be assisted by matching overlaps from reads that came from the same molecule; and complementary reads from the same molecule can be used to error check the reads and confirm rare variants.

Example II

Algorithms for Determining Phase for Sequenced Fragments

Target nucleic acids can be processed to create an array of fragments, wherein the proximity of fragments to each other on the array is directly correlated with the probability that the fragments were produced from the same target nucleic acid molecule. The processing can be carried out as set forth in Example I or elsewhere herein.

In one embodiment, the process starts with target nucleic acids that have been isolated from a biological source using gentle preparation methods to minimize damage to genomic DNA (gDNA), so as to preserve the length of target gDNA molecules to the extent possible. Each target gDNA is modified to add inserts. A library of modified gDNA polymers is delivered to a MiSeq flow cell (Illumina, Inc. San Diego, Calif.) and allowed to diffuse to achieve separation between library members. The modified gDNAs are fragmented in the flow cell such that each modified gDNA polymer produces a sublibrary of gDNA fragments that are captured randomly at locations on the surface of the flow cell. Conditions are used to allow fragments from each modified gDNA to be captured within proximity of each other. Clusters are grown from each fragment at the respective locations. The clusters are sequenced using standard MiSeq protocols (Illumina, Inc, San Diego, Calif.).

The sum of the sequences present in a gDNA fragment sublibraries can constitute a fraction of the gDNA sequence of the biological source or it can cover the entirety of the gDNA sequence at least 1×. Typically, the complete set of gDNA fragments will cover the entirety of the gDNA sequence multiply, for example, by at least 10× or more. The sequences of the gDNA fragments in the complete set, when aligned to the entire gDNA sequence, can be abutted, overlapping or gapped.

Proximity of surface-attached fragments (or clusters derived from fragments) can be treated as a characterization of the physical distance between sublibrary members. Although proximity is a measure of "closeness," the surface-attached fragments (or clusters) should be spaced far enough apart that they are resolvable by the sequencing platform detector. This resolution is desired both for fragments from different gDNA fragment sublibraries (i.e. inter) and those from the same sublibrary (i.e. intra).

For purposes of analysis, members of a given sublibrary are considered "in proximity" on a surface if the spatial distances among the members is much less than the spatial distance to the nearest sublibrary coming from adjacent region of the genome. For example, looking at FIG. 3, the clusters of the gamma sublibrary are considered to be "in proximity" to each other despite the fact that some of the clusters in the gamma sublibrary are closer to clusters in the nearby beta sublibrary than they are to clusters in their own sublibrary. The clusters of the gamma sublibrary are considered to be "in proximity" because the beta sublibrary, despite appearing to be physically proximal to the gamma sublibrary on the surface, can be identified by sequence analysis to be derived from a region of the gDNA sequence that is far away (i.e. the alpha and gamma sublibraries are derived from regions that are far from each other in the target genome).

An algorithm for determining sequences of fragments that are connected in the target gDNA can include the following steps;
(a) sequence reads are obtained for clusters on the surface;
(b) the sequence reads are aligned to a reference genome and variants are identified;
(c) a sliding window (e.g. 100 Kb) is used along the genome to reduce the number of reads to be analyzed;
(d) density based spatial clustering algorithm is used to identify clouds (i.e. regions) of clusters that are "in proximity";
(e) a virtual barcode is assigned to each of the clouds (i.e. reads derived from the same cloud have the same barcode and barcodes are unique between different clouds); and
(f) the barcoded reads are analyzed through the ReFHap software (Duitama et al. Proceeding of the First ACM International Conference on Bioinformatics and Computational Biology Pages 160-169 (2010), which is incorporated herein by reference) to determine phasing of the identified variants.

An alternative algorithm for determining connectivity can include steps (a) and (b) of the above algorithm followed by use of a version of the ReFHap software that has been altered to use a distance metric. An exemplary distance metric places a greater weight on two SNPs with a shorter distance from each other (i.e. proximal) than SNPs which are distant from each other.

Example III

Metagenomic Applications

In this example proximity mapping is used to call sequence reads as belonging to a single organism in a mixed sample of various organisms. Thus, the mixed sample can be thought of as being analogous to the mix of the maternal and paternal haplotypes that are distinguished in a haplotyping or phasing application.

A workflow is carried out as follows:
- (a) Extract DNA from the organisms in a mixed sample.
- (b) Optionally, enrich for desired targets or deplete sample of "known and/or uninteresting" organisms. This can be done for example using targeted amplification methods to selectively amplify only a portion of a nucleic acid sample as set forth previously herein.
- (c) Prepare DNA with transpososme complexes as set forth in Example I or elsewhere herein.
- (d) Seed the DNA prepared in step (c) into flowcell as set forth in Example I or elsewhere herein.
- (e) Clusters/sequence reads in proximity to each other will have a certain probability to have come from the same original organism.
- (f) Optionally, filter out reads which align to "known and uninteresting" organisms (i.e. during secondary sequence analysis), thus reducing the effective "density" of the noise surrounding clouds of proximal fragments.
- (g) This information can then assist in the building of assembly scaffolds for the genomes of each organism in the sample.

An alternative workflow could be used to capture the organisms themselves at a location in the flowcell, and then perform the sample prep described in steps (b) through (d) in situ. In this way substantially all of the recoverable DNA from an organism is localized to a given spatial location in the flowcell, instead of just long sections from it.

Figure 9:
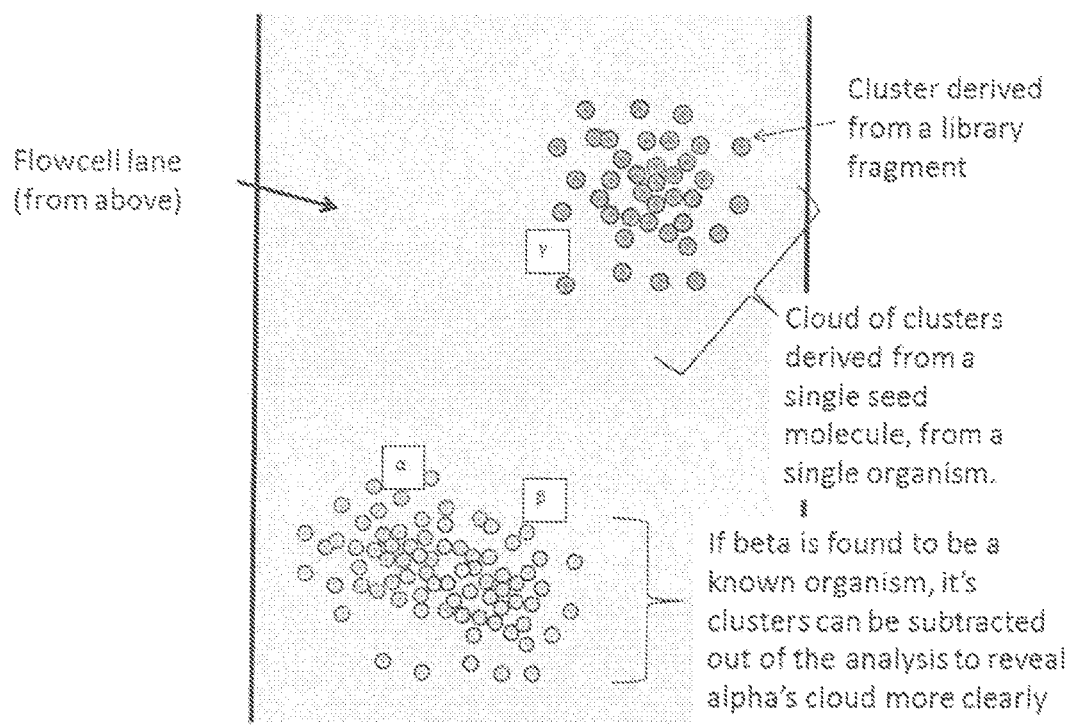
FIG. 9 shows a diagram of cluster clouds resulting from the nucleic acid fragments captured from a metagenomic sample on a flow cell and subsequently bridge amplified.

A diagram of results that can result is shown in FIG. 9. Three different cluster clouds derived from three different organisms in a metagenomic sample are shown. The clouds are identified as α, β, or γ. As exemplified for the α and β clouds, when two clouds overlap, the fragments that align with a known organism (for example, the beta organism) can be subtracted or removed from the analysis to more clearly identify the sequences derived from the alpha organism.

Example IV

Generating Proximity Reads on Flow Cells

Figure 10:
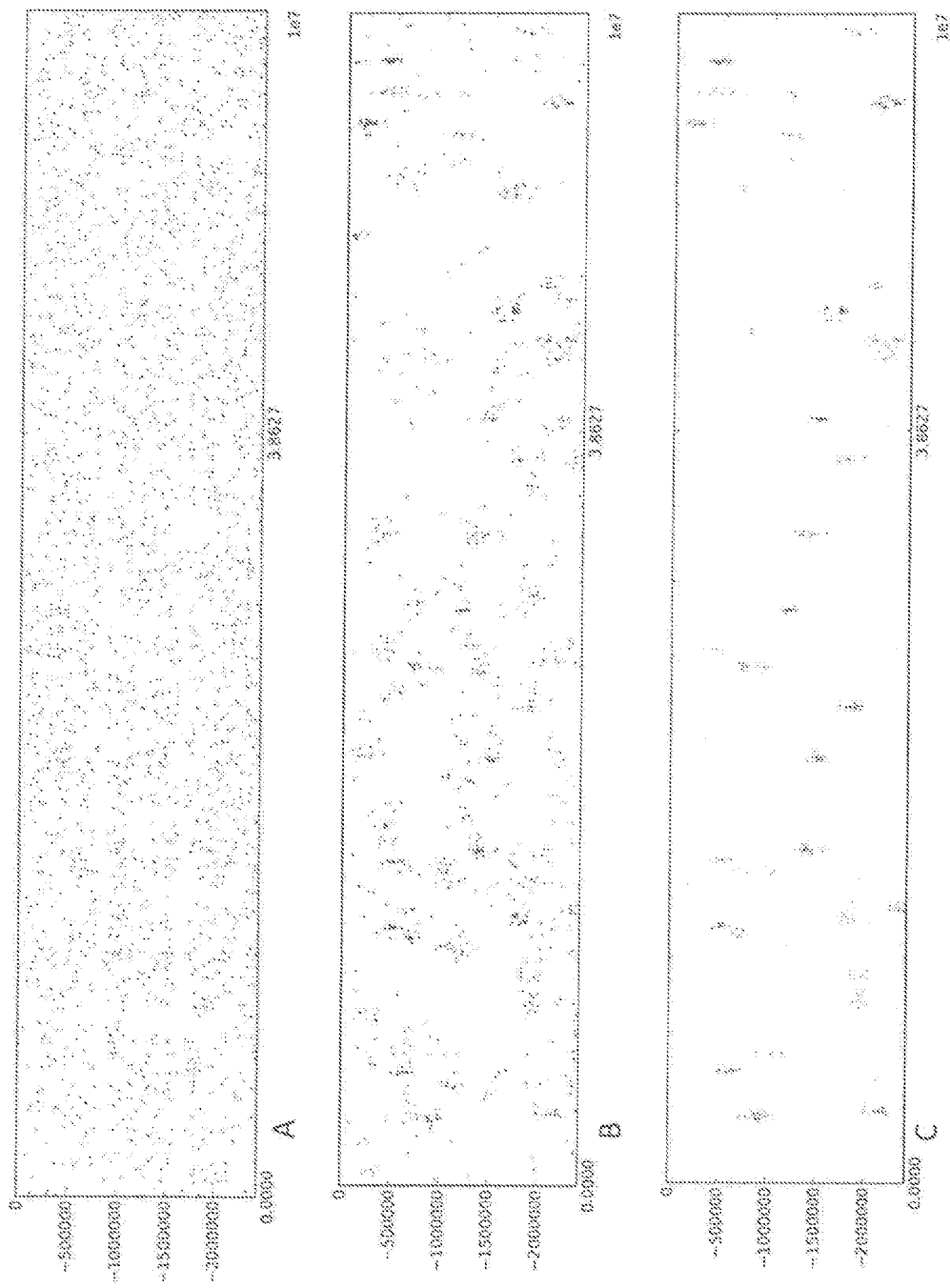
FIG. 10 shows a spatial distribution of sequencing clusters in a flow cell. The control lane (A), which was prepared without using the proposed method, shows no correlation among clusters' spatial locations; they are evenly distributed over the area of the flow cell. The lane prepared using the proposed method (B) shows the sequencing clusters forming spatially co-located groups, which were identified by automated algorithms and assigned to sets (C) for phasing or assembly based on proximity. All units in nanometers. The X- and the Y-axis are in nm.

Promiximity reads on flow cells were generated using 50 ng of genomic DNA in 10 ul of buffer. Transposition mix components (Tn5 complexes, MgCl, Tris buffer) were added to the DNA for a final 20 ul reaction mix, and heated to 55 C for 10 minutes. The DNA was diluted to 50 pM concentration (based on average fragment size) and the DNA still bound to transpososomes was loaded onto flow cell The transposase enzyme was removed from the DNA using SDS, and the gaps were repaired using a polymerase/ligase mix. The fragments were allowed to seed to flow cell surface in proximity to initial capture site. Bridge amplification was performed to amplify fragments in place to form clonal clusters. Sequencing of the amplified DNA was performed. Sequencing data was analyzed to identify proximal groups of clusters, to infer which fragments were derived from the same original molecule of DNA. This information was then used to determine the phase of SNPs in the sample and shown in FIG. 10.

Human genomic DNA (Coriell sample NA12878) was prepared using the proposed method and sequenced on an Illumina HiSeq platform. Twelve indices were added to the sample preparation to allow for higher density clustering and more accurate identification of the proximal groups. After alignment to a reference genome (HG19), data from 2 or 3 lanes were combined and analyzed for proximal groups of clusters. Information from the proximal groups was then used to determine the phase of heterogeneous SNPs in the sample. The phasing data was shown in Table 1 below.

TABLE 1

Phasing Data
Sample: Human DNA, Coriell NA12878

|  | 2 Hiseq Lanes | 3 Hiseq Lanes |
|---|---|---|
| Clusters passing filter | 418M | 642M |
| Chr1 clusters | 28.5M | 42.2M |
| Chr1 clusters in proximal groups | 19.7M | 29.9M |
| Chr1 groups | 648k | 1.0M |
| % of Chr1 SNPs phased | 93% | 97% |
| Edit error rate | 1.8% | 3% |
| Switch error rate | 0.5% | 0.2% |

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of sequencing a target nucleic acid polymer, comprising:
   (a) modifying a target nucleic acid polymer to produce a modified nucleic acid polymer, wherein the modified nucleic acid polymer comprises a plurality of sequence regions from the target nucleic acid polymer;
   (b) releasing fragments of the modified nucleic acid polymer onto a solid support surface, each fragment comprising one of the sequence regions;
   (c) capturing the fragments randomly at locations in an area of the solid support surface;
   (d) determining nucleotide sequences of the sequence regions by detecting the fragments at the locations;
   (e) determining relative physical distances between the fragments at the locations; and
   (f) producing a representation of the nucleotide sequence for the target nucleic acid polymer based on the nucleotide sequences from the fragments and the determined relative physical distances between the locations on the solid support surface, wherein the relative physical distances are indicative of distances between the sequence regions along a given strand of the target nucleic acid polymer.

2. The method of claim 1, wherein the modifying comprises adding inserts into the target nucleic acid polymer to form the modified nucleic acid polymer, wherein the modified nucleic acid polymer comprises a plurality of internal inserts.

3. The method of claim 2, wherein the fragments produced in step (b) each comprise at least a portion of an insert added in step (a).

4. The method of claim 3, wherein the inserts further comprise cleavage sites and wherein producing of the fragments in step (b) comprises cleaving the inserts at the cleavage sites.

5. The method of claim 2, wherein the inserts have priming sites; wherein the fragments each comprise at least a portion of the inserts having the priming sites; and wherein step (d) comprises determining nucleotide sequences from the fragments by extension of primers hybridized to the priming sites at the locations.

6. The method of claim 2, wherein the inserts comprise ligands that attach to receptors on the solid support surface.

7. The method of claim 2, wherein the inserts are added into the target nucleic acid polymer by transposases.

8. The method of claim 7, wherein each of the inserts comprise a first transposon element and a second transposon element that is contiguous with the first transposon element; and wherein a transposase associated with the first transposon element and the second transposon element forms a transposome.

9. The method of claim 8, wherein the 5' end of the first transposon element is attached to the 5' end of the second transposon element by a linker.

10. The method of claim 8, wherein the first transposon element and the second transposon element each comprise a forked adapter.

11. The method of claim 8, wherein the transposases comprise ligands and the surface comprises receptors that bind to the ligands to attach the modified nucleic acid polymer to the surface prior to the producing of the fragments.

12. The method of claim 7, wherein step (b) comprises attaching the modified nucleic acid polymer to the solid support surface prior to the producing of the fragments.

13. The method of claim 12, wherein the transposases are removed from the modified nucleic acid polymer prior to the attaching of the modified nucleic acid polymer to the solid support surface.

14. The method of claim 12, wherein the transposases are removed from the modified nucleic acid polymer after the attaching of the modified nucleic acid polymer to the solid support surface.

15. The method of claim 14, wherein the modified nucleic acid polymer is attached to the solid support surface via binding of at least one transposase to the surface.

16. The method of claim 1, wherein the determining of nucleotide sequences comprises nanopore sequencing.

17. The method of claim 1, wherein step (a) comprises modifying a plurality of different target nucleic acid polymers to produce a mixture of modified nucleic acid polymers, wherein each of the modified nucleic acid polymers comprises a plurality of sequence regions from an individual target nucleic acid polymer of the plurality of different target nucleic acid polymers.

18. The method of claim 17, wherein step (e) comprises producing representations of the nucleotide sequences for the target nucleic acid polymers based on the nucleotide sequences from the fragments and the relative distances between the locations on the solid support surface.

19. The method of claim 1, wherein the solid support surface comprises an interior surface of a flow cell.

20. The method of claim 1, further comprising determining haplotype phase for polymorphisms occurring in the nucleotide sequences for different fragments released from the modified nucleic acid polymer.

21. A method of sequencing a target nucleic acid polymer, comprising:
    (a) modifying a target nucleic acid polymer to produce a modified nucleic acid polymer, wherein the modified nucleic acid polymer comprises a plurality of sequence regions from the target nucleic acid polymer;
    (b) attaching the modified nucleic acid polymer to an area on a solid support surface;
    (c) producing fragments of the modified nucleic acid polymer that is attached to the solid support surface, wherein the fragments are attached to locations at the area on the solid support surface;
    (d) determining nucleotide sequences from the fragments by detecting the fragments at the locations;
    (e) determining relative physical distances between the fragments at the locations; and
    (f) producing a representation of the nucleotide sequence for the target nucleic acid polymers based on the nucleotide sequences from the fragments and the determined relative physical distances between the locations on the solid support surface, wherein the relative physical distances are indicative of distances between the sequence regions along a given strand of the target nucleic acid polymer.

22. A method of sequencing a target nucleic acid polymer, comprising:
    (a) adding inserts into a target nucleic acid polymer to form a modified nucleic acid polymer comprising a plurality of internal inserts;
    (b) producing fragments of the modified nucleic acid polymer in a fluid that is in contact with a solid support surface, thereby releasing fragments that each comprise at least a portion of the inserts having the priming sites;
    (c) capturing the fragments from the fluid randomly at locations on the solid support surface;
    (d) determining nucleotide sequences from the fragments by detecting the fragments at the locations;
    (e) determining relative physical distances between the fragments at the locations; and
    (f) producing a representation of the nucleotide sequence for the target nucleic acid polymer based on the nucleotide sequences from the fragments and the determined relative physical distances between the locations on the solid support surface, wherein the relative physical distances are indicative of distances between sequence regions along a given strand of the target nucleic acid polymer.

23. A method of sequencing a target nucleic acid polymer, comprising:
    (a) adding inserts into a target nucleic acid polymer to form a modified nucleic acid polymer comprising a plurality of internal inserts, wherein the inserts have priming sites;
    (b) producing fragments of the modified nucleic acid polymer in a fluid that is in contact with the solid support surface, thereby releasing fragments that each comprise at least a portion of the inserts having the priming sites;
    (c) capturing the fragments from the fluid randomly at locations on a solid support surface;
    (d) determining nucleotide sequences from the fragments by extension of primers hybridized to the priming sites at the locations;
    (e) determining relative physical distances between the fragments at the locations; and
    (f) producing a representation of the nucleotide sequence for the target nucleic acid polymer based on the nucleotide sequences from the fragments and the determined relative physical distances between the locations on the solid support surface, wherein the relative physical distances are indicative of distances between sequence regions along a given strand of the target nucleic acid polymer.

24. A method of sequencing a target nucleic acid polymer, comprising:
    (a) adding inserts into a target nucleic acid polymer to form a modified nucleic acid polymer comprising a plurality of internal inserts;
    (b) attaching the modified nucleic acid polymer to a solid support surface;
    (c) producing fragments of the modified nucleic acid polymer that is attached to the solid support surface, wherein the fragments are attached to locations on the solid support surface and wherein the fragments each comprise at least a portion of the inserts;
    (d) determining nucleotide sequences from the fragments by detecting the fragments at the locations;
    (e) determining relative physical distances between the fragments at the locations; and
    (f) producing a representation of the nucleotide sequence for the target nucleic acid polymer based on the nucleotide sequences from the fragments and the determined relative physical distances between the locations on the solid support surface, wherein the relative physical distances are indicative of distances between sequence regions along a given strand of the target nucleic acid polymer.

25. A method of determining the source of individual sequences in a mixture of sequences from different sources, comprising:
    (a) providing a mixture of target nucleic acid polymers from a plurality of different sources;
    (b) modifying the mixture of target nucleic acid polymers to produce a mixture of modified nucleic acid polymers, wherein the mixture of modified nucleic acid polymers comprises a plurality of sequence regions from the different sources;
    (c) producing fragments of the modified nucleic acid polymers in a vessel having a solid support surface, each fragment comprising a sequence region from a single one of the different sources;
    (d) capturing the fragments randomly at locations of the solid support surface, under conditions wherein fragments from a common target nucleic acid polymer preferentially localize to proximal locations on the solid support surface;
(e) determining nucleotide sequences of the fragments at the locations;
(f) determining relative physical distances between the fragments at the locations; and
(g) identifying the nucleotide sequences from the mixture of target nucleic acid polymers that are derived from a common source from the plurality of different sources based on the nucleotide sequences from the fragments and the determined relative physical distances between the locations on the solid support surface, wherein the relative physical distances are indicative of distances between the sequence regions along a given strand of a target nucleic acid polymer from the mixture of target nucleic acid polymers.

26. A method of determining the source for individual sequences in a mixture of sequences from different sources, comprising:
(a) providing a mixture of target nucleic acid polymers from a plurality of different sources;
(b) modifying the mixture of target nucleic acid polymers to produce a mixture of modified nucleic acid polymers, wherein the mixture of modified nucleic acid polymers comprises a plurality of sequence regions from the different sources;
(c) attaching the modified nucleic acid polymers to a solid support surface;
(d) producing fragments of the modified nucleic acid polymers that are attached to the solid support surface, wherein fragments from a common source of the plurality of sources are attached to locations that are proximal on the solid support surface;
(e) determining nucleotide sequences of the fragments at the locations;
(f) determining relative physical distances between the fragments at the locations; and
(g) identifying the nucleotide sequences from the mixture of target nucleic acid polymers that are derived from a common source from the plurality of different sources based on the nucleotide sequences from the fragments and the determined relative physical distances between the locations on the solid support surface, wherein the relative physical distances are indicative of distances between the sequence regions along a given strand of a target nucleic acid polymer from the mixture of target nucleic acid polymers.

27. A method of determining the source for individual sequences in a mixture of sequences from different sources, comprising:
(a) providing a mixture of target nucleic acid polymers from a plurality of different sources;
(b) adding inserts into the target nucleic acid polymers in the mixture to form a mixture of modified nucleic acid polymers, each polymer including a plurality of internal inserts;
(c) producing fragments of the modified nucleic acid polymers in a fluid that is in contact with a solid support surface, thereby releasing fragments that each include at least a portion of each of the inserts;
(d) capturing the fragments from the fluid randomly at locations on the solid support surface;
(e) determining nucleotide sequences from the fragments by detecting the fragments at the locations;
(f) determining relative physical distances between the fragments at the locations;
(g) identifying the nucleotide sequences from the mixture of target nucleic acid polymers that are derived from a common source from the plurality of different sources based on the nucleotide sequences from the fragments and the determined relative physical distances between the locations on the solid support surface, wherein the relative physical distances are indicative of distances between sequence regions along a given strand of a target nucleic acid polymer from the mixture of target nucleic acid polymers.

28. A method of determining the source for individual sequences in a mixture of sequences from different sources, comprising:
(a) providing a mixture of target nucleic acid polymers from a plurality of different sources;
(b) adding inserts into the target nucleic acid polymers in the mixture to form a mixture of modified nucleic acid polymers, each polymer comprising a plurality of internal inserts;
(c) attaching the modified nucleic acid polymer to a solid support surface;
(d) producing fragments of the modified nucleic acid polymers that are attached to the solid support surface, wherein fragments from a common source of the plurality of sources are attached to locations that are proximal on the solid support surface;
(e) determining nucleotide sequences from the fragments by detecting the fragments at the locations;
(f) determining relative physical distances between the fragments at the locations; and
(g) identifying the nucleotide sequences from the mixture of target nucleic acid polymers that are derived from a common source from the plurality of different sources based on the nucleotide sequences from the fragments and the determined relative physical distances between the locations on the solid support surface, wherein the relative physical distances are indicative of distances between sequence regions along a given strand of a target nucleic acid polymer from the mixture of target nucleic acid polymers.

29. The method of claim 1, wherein step (f) comprises determining that two of the fragments are derived from a common source based on the relative physical distances.

30. The method of claim 29, wherein step (f) comprises determining that the two fragments derived from the common source have closer relative physical distances than other fragments that are not derived from the common source.

31. The method of claim 1, wherein step (e) comprises generating a map of clusters at the locations.

32. The method of claim 1, wherein step (f) comprises determining the distances between fragments in a plurality of overlapping fragments.

33. The method of claim 32, wherein step (f) comprises determining that overlapping fragments are derived from different common sources based on determined relative distances between the plurality of overlapping fragments.

34. The method of claim 21, wherein step (f) comprises determining that two of the fragments are derived from a common source based on the determined relative physical distances and comparison of the nucleotide sequences of the two fragments with a reference sequence.

35. The method of claim 1, wherein the distances are genomic distances.

36. The method of claim 1, wherein the fragments of the modified nucleic acid polymer are closer in relative physical distance to one another than other fragments of another modified nucleic acid polymer captured on the solid support surface.

* * * * *